(12) United States Patent
Munson et al.

(10) Patent No.: US 8,026,233 B2
(45) Date of Patent: Sep. 27, 2011

(54) P38 INHIBITORS AND METHODS OF USE THEREOF

(75) Inventors: Mark C. Munson, Louisville, CO (US); Kevin W. Hunt, Longmont, CO (US); Christopher T. Clark, Westminster, CO (US); Ganghyeok Kim, Superior, CO (US); Laurence E. Burgess, Boulder, CO (US); James P. Rizzi, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 284 days.

(21) Appl. No.: 12/294,550

(22) PCT Filed: Mar. 27, 2007

(86) PCT No.: PCT/US2007/007658
§ 371 (c)(1),
(2), (4) Date: Sep. 25, 2008

(87) PCT Pub. No.: WO2007/126871
PCT Pub. Date: Nov. 8, 2007

(65) Prior Publication Data
US 2009/0149443 A1    Jun. 11, 2009

Related U.S. Application Data

(60) Provisional application No. 60/786,962, filed on Mar. 29, 2006.

(51) Int. Cl.
C07D 403/12 (2006.01)
C07D 401/12 (2006.01)
A61K 31/416 (2006.01)

(52) U.S. Cl. ............ 514/212.08; 514/322; 514/338; 514/406; 540/524; 546/199; 546/256; 548/362.5

(58) Field of Classification Search .......... 514/212.08, 514/322, 338, 406; 540/524; 546/199, 256; 548/362.5
See application file for complete search history.

(56) References Cited

U.S. PATENT DOCUMENTS
2004/0192654 A1    9/2004 Munson et al.

*Primary Examiner* — Bruck Kifle
(74) *Attorney, Agent, or Firm* — John R. Moore, Esq.; Sarah S. Mastous

(57) ABSTRACT

Compounds of formula (I): in which A, B, X, $Ar^1$, $R^8$ and $R^4$ have any of the meanings given in the specification, are inhibitors of p38 useful in the treatment and prevention of various disorders mediated by p38.

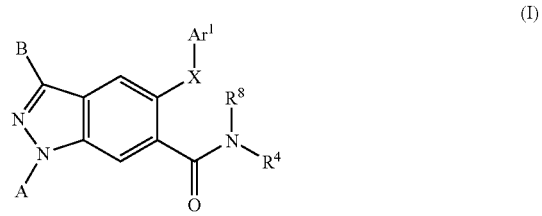

19 Claims, No Drawings

P38 INHIBITORS AND METHODS OF USE THEREOF

This application claims the benefit of United States provisional patent application No. 60/786,962 filed on Mar. 29, 2006, which is incorporated herein by reference in its entirety.

BACKGROUND OF THE INVENTION

1. Field of the Invention

This invention relates to inhibitors of p38 MAPK and related kinases, pharmaceutical compositions containing the inhibitors, and methods for preparing these inhibitors. The p38 inhibitors of this invention are useful for the treatment of p38 MAPK-mediated diseases and conditions.

2. Description of the State of the Art

A number of chronic and acute inflammatory conditions have been associated with the overproduction of pro-inflammatory cytokines. Such cytokines include but are not limited to tumor necrosis factor alpha (TNF-α), interleukin 1 beta (IL-1β), interleukin 8 (IL-8) and interleukin 6 (IL-6). Rheumatoid arthritis (RA) is a chronic disease where TNF-α and IL-1β are implicated in the onset of the diseases and in the progression of the bone and joint destruction seen with this debilitating condition. Recently approved therapeutic treatments for RA have included soluble TNF-α receptor (ENBREL™) and IL-1 receptor antagonist (ANAKINRA™). These treatments work by blocking the ability of their respective cytokines to bind to their natural receptors. Alternative methods for treating cytokine-mediated diseases are currently under investigation. One such method involves inhibition of the signaling pathway that regulates the synthesis and production of pro-inflammatory cytokines such as p38.

P38 (also known as CSBP or RK) is a serine/threonine mitogen-activated protein kinase (MAPK) that has been shown to regulate pro-inflammatory cytokines. P38 MAPK was first identified as a kinase that becomes tyrosine phosphorylated in mouse monocytes following treatment with lipopolysaccharide (LPS). A link between p38 MAPK and the response of cells to cytokines was first established by Saklatvala et al., (Cell, 1994, 78:1039-1049), who showed that IL-1 activates a protein kinase cascade that results in the phosphorylation of the small heat shock protein, Hsp27, probably by mitogen-activated protein activated protein kinase 2 (MAPKAP kinase-2). Analysis of peptide sequences derived from the purified kinase indicated that it was related to the p38 MAPK activated by LPS in mouse monocytes (Han, J., et al., Science, 1994, 265:808-811). At the same time it was shown that p38 MAPK was itself activated by an upstream kinase in response to a variety of cellular stresses, including exposure to UV radiation and osmotic shock, and the identity of the kinase that directly phosphorylates Hsp27 was confirmed as MAPKAP kinase-2 (Rouse, J., et al., Cell, 1994, 78:1027-1037). Subsequently, it was shown that p38 MAPK was the molecular target of a series of pyridinylimidazole compounds that inhibited the production of TNF from LPS-challenged human monocytes (Lee, J., et al., Nature, 372:739-746). This was a key discovery, which has led to the development of a number of selective inhibitors of p38. MAPK and the elucidation of its role in cytokine signaling.

It is now known that multiple forms of p38 MAPK (α, β, γ, δ), each encoded by a separate gene, form part of a kinase cascade involved in the response of cells to a variety of stimuli, including osmotic stress, UV light, and cytokine mediated events. These four isoforms of p38 are thought to regulate different aspects of intracellular signaling. Activation of p38 is part of a cascade of signaling events that lead to the synthesis and production of pro-inflammatory cytokines such as TNF-α. P38 functions by phosphorylating downstream substrates that include other kinases and transcription factors. Agents that inhibit p38 MAPK have been shown to block the production of cytokines including, but not limited to, TNF-α, IL-6, IL-8 and IL-1β in vitro and in vivo models (Adams, J. L., et al., Progress in Medicinal Chemistry, 2001, 38:1-60).

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS (Lee, J. C., et al., Int. J. Immunopharmacol., 1988, 10:835-843). The efficacy of p38 inhibitors in animal models of inflammatory disease has prompted an investigation of the underlying mechanism(s) which could account for the effect of these inhibitors. The role of p38 in the response of cells to IL-1 and TNF has been investigated in a number of cells systems relevant to the inflammatory response using a pyridinyl imidazole inhibitor, such as: endothelial cells and IL-8 (Hashimoto, S., et al., J. Pharmacol. Exp. Ther., 2001, 293:370-375), fibroblasts and IL-6/GM-CSF/PGE2 (Beyaert, R., et al., EMBO J., 1996, 15:1914-1923), neutrophils and IL-8 (Albanyan, E. A., et al., Infect. Immun., 2000, 68:2053-2060) macrophages and IL-1 (Caivano, M. and Cohen, P., J. Immunol., 2000, 164:3018-3025), and smooth muscle cells and RANTES (Maruoka, S., et al., Am. J. Respir. Crit. Care Med., 1999, 161:659-668). The destructive effects of many disease states are caused by the over production of pro-inflammatory cytokines. The ability of p38 inhibitors to regulate this overproduction makes them excellent candidates for disease modifying agents.

Known inhibitors of p38 MAPK are active in a variety of widely recognized disease models. Inhibitors of p38 MAPK show positive effects in a number of standard animal models of inflammation including rat collagen-induced arthritis (Jackson, J. R., et al., J. Pharmacol. Exp. Ther., 1998, 284:687-692); rat adjuvant-induced arthritis to (Badger, A. M., et al., Arthritis Rheum., 2000, 43:175-183; Badger, A. M., et al., J. Pharmacol. Exp. Ther., (1996) 279:1453-1461); and carrageenan-induced paw edema in the mouse (Nishikori, T., et al., Eur. J. Pharm., 2002, 451:327-333). Molecules that block the function of p38 have been shown to be effective in inhibiting bone resorption, inflammation, and other immune and inflammation-based pathologies in these animal models. Thus, a safe and effective p38 inhibitor would provide a means to treat debilitating diseases that can be regulated by modulation of p38 signaling such as, but not limited to, rheumatoid arthritis (RA).

P38 MAPK inhibitors are well known to those skilled in the art. Reviews of early inhibitors have helped establish the structure activity relationships important for enhanced activity both in vitro and in vivo (see, e.g., Salituro, E. G., et al., Current Medicinal Chemistry, (1999) 6:807-823 and Foster, M. L., et al., Drug News Perspect., 2000, 13:488-497). More contemporary reviews have focused on the structural diversity of new inhibitors being explored as p38 inhibitors (Boehm, J. D. and Adams, J. L., Exp. Opin. Ther. Patents, 2000, 10:25-37).

International patent application, publication number WO 04/078116 discloses certain compounds as p38 inhibitors.

It has now been found that one of the compounds exemplified in WO 04/078116 is metabolized in vivo to afford a metabolite that is itself active as a p38 inhibitor. This, in turn has led to the finding of further novel p38 inhibitors.

SUMMARY OF THE INVENTION

This invention provides compounds that inhibit p38 MAPK and associated p38 mediated events such as cytokine production. Such compounds have utility as therapeutic agents for diseases that can be treated by the inhibition of the p38 MAPK signaling pathway.

In general, one aspect of the invention relates to compounds of the general Formula I:

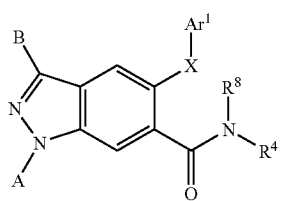

I and enantiomers, diastereomers, solvates, metabolites and salts thereof, wherein A, B, X, $R^4$, $R^8$ and $Ar^1$ are as defined herein.

A further aspect of this invention provides a method of treating diseases or medical conditions in a mammal mediated by cytokines, which comprises administering to said mammal a therapeutically effective amount of a compound of the invention.

A further aspect of this invention provides a method of providing a p38 MAPK inhibitory effect in a mammal, comprising administering to said mammal a therapeutically effective amount of a compound of this invention.

A further aspect of this invention provides treating or preventing a p38 kinase-mediated condition in a mammal, comprising administering a therapeutically effective amount of a compound of this invention. P38-kinase-mediated conditions that can be treated according to the methods of this invention include, but are not limited to, inflammatory diseases, autoimmune diseases, destructive bone disorders, hyperproliferative disorders, infectious diseases, viral diseases, and neurodegenerative disease.

A further aspect of this invention provides methods of inhibiting the production of cytokines such as TNF-α, IL-1, IL-6 and IL-8 in a mammal, comprising administering to said mammal a therapeutically effective amount of a compound of this invention.

The compounds of this invention are also useful in methods for preventing cell death and hyperplasia and therefore may be used to treat or prevent reperfusion/ischemia in stroke, heart attacks, and organ hypoxia. The compounds of this invention are also useful in methods for preventing thrombin-induced platelet aggregation.

The invention also relates to pharmaceutical compositions comprising a compound of this invention and a pharmaceutically acceptable carrier.

The compounds of this invention may be used advantageously in combination with other known therapeutic agents.

In a further aspect this invention provides compounds of this invention for use in therapy.

An additional aspect of the invention is the use of a compound of this invention in the preparation of a medicament for use as a p38 kinase inhibitor.

This invention further provides kits for the treatment or prevention of a p38 kinase-mediated disease or disorder, comprising a compound of this invention, a container, and a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of this invention as defined by the claims. One skilled in the art will recognize many methods and materials similar or equivalent to those described herein, which could be used in the practice of this invention. This invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "haloalkyl" as used herein refers to an alkyl group wherein one or more of the hydrogens is replaced by a halogen as defined below, which replacement can be at any site on the alkyl, including the end. Examples include, but are not limited to, $CH_2F$, $CHF_2$, $CF_3$, $CH_2CH_2F$, $CH_2CHF_2$, $CH_2CF_3$, $CHFCF_3$, $CF_2CF_3$, $CH_2Cl$, $CHCl_2$, $CCl_3$, $CH_2CH_2Cl$, $CH_2CHCl_2$, $CH_2CCl_3$, $CHClCCl_3$, $CCl_2CCl_3$, etc.

The term "alkenyl" as used herein refers to a linear or branched-chain monovalent hydrocarbon radical of two to twelve carbon atoms with at least one site of unsaturation, i.e., a carbon-carbon, $sp^2$ double bond, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), 1-propenyl, 1-buten-1-yl, 1-buten-2-yl, and the like.

The term "alkynyl" as used herein refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH) and propynyl (propargyl, —CH$_2$C≡CH).

The terms "cycloalkyl," and "carbocyclic ring" as used herein are used interchangeably and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, and the like. Bicyclic carbocycles include those having 7 to 12 ring atoms arranged, for example, as a bicyclo [4,5], [5,5], [5,6] or [6,6] system, or as bridged systems such as bicyclo[2.2.1]heptane, bicyclo[2.2.2]octane, and bicyclo[3.2.2]nonane.

"Aryl" as used herein means a monovalent aromatic (fully unsaturated) hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronaphthalene, 1,2,3,4-tetrahydronaphthalene, and the like.

The terms "heterocycle", "heterocyclyl" and "heterocyclic ring" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" as used herein includes fluorine (F), bromine (Br), chlorine (Cl), and iodine (I).

An "amine protecting group" is a substituent attached to an amino group that blocks or protects the amino functionality in the compound. Examples of amine protecting groups include, but are not limited to, acetyl, trifluoroacetyl, t-butoxycarbonyl (BOC), benzyloxycarbonyl (CBZ) and 9-fluorenylmethylenoxycarbonyl (Fmoc).

The term "a" as used herein means one or more.

As used herein, the terms "compound of this invention," and "compounds of the present invention" include compounds of Formula I tautomers, resolved enantiomers, resolved diastereomers, racemic mixtures, solvates, metabolites, salts and prodrugs thereof, including pharmaceutically acceptable salts and prodrugs.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

This invention provides compounds of this invention are useful for inhibiting p38 MAPK and associated kinase-mediated events such as cytokine production. Such compounds have utility as therapeutic agents for diseases that can be treated by the inhibition of a kinase signaling pathway.

In one aspect, the present invention provides compounds of Formula I:

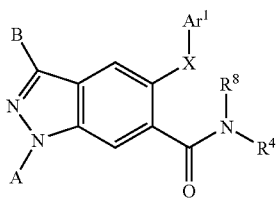

I and enantiomers, diastereomers, solvates, metabolites and salts thereof, wherein:

X is O, S, SO, $SO_2$, $NR^7$, C=O, $CR^7R^{7a}$, C=$NOR^1$, C=$CHR^1$ or $CHOR^1$;

$Ar^1$ is a 5- or 6-membered aryl or heteroaryl ring, wherein said aryl and heteroaryl are optionally substituted with one or more groups independently selected from $NH_2$, NHMe, $NMe_2$, $CH_2OH$, cyclopropyl, $C_1$-$C_3$ alkyl, $C_1$-$C_3$ haloalkyl, OH, CN, F, Cl, Br I, $SCH_3$, $OCH_3$, and $OCF_3$;

A is H, an amine protecting group, $C_1$-$C_{12}$ alkyl, $C_2$-$C_{12}$ alkenyl, $C_2$-$C_{12}$ alkynyl, saturated or partially unsaturated cycloalkyl, saturated or partially unsaturated heterocyclyl, aryl or heteroaryl, wherein said alkyl, alkenyl, alkynyl, cycloalkyl, heterocyclyl, aryl and heteroaryl are optionally substituted with one or more groups independently selected from F, Cl, Br, I, CN, =O, =$NOR^{16}$, $NR^{16}R^{17}$, $NR^{16}$(C=O) $R^{17}$, $NR^{16}$C(=O)$NR^{17}R^{18}$, $NR^{16}$C(=O)$R^{17}$, OC(=O) $NR^{16}R^{17}$, $CR^{17}$=$NOR^{16}$, $SO_2R^{19}$, $SOR^{17}$, $SR^{17}$, $SO_2NR^{16}R^{17}$, $OR^{16}$, (C=O)$R^{16}$, (C=O)$OR^{16}$, O—(C=O) $R^{16}$, $C_1$-$C_6$ alkyl, $C_2$-$C_6$ alkenyl, $C_2$-$C_6$ alkynyl, saturated or partially unsaturated cycloalkyl, saturated or partially unsaturated heterocyclyl, and a 5- or 6-membered heteroaryl or aryl ring;

B is H, $NH_2$, NHMe, $NMe_2$, $CH_3$, $CH_2OH$, cyclopropyl, $C_1$-$C_3$ alkyl, OH, CN, F, Cl, Br or I, wherein said alkyl is optionally substituted with one or more groups independently selected from F, Cl, Br and I;

$R^1$ is H, $C_1$-$C_{12}$ alkyl, $C_2$-$C_{12}$ alkenyl, $C_2$-$C_{12}$ alkynyl;

$R^4$ is

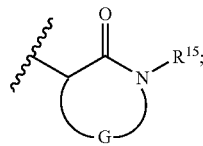

G is a $C_2$-$C_4$ hydrocarbon chain, which taken together with the atoms to which it is attached, forms a 5 to 7 membered saturated or unsaturated ring that is optionally substituted with one or more $R^{30}$ groups;

$R^7$ and $R^{7a}$ are independently H or $C_1$-$C_{12}$ alkyl, or $R^7$ and $R^{7a}$ together with the carbon to which they are attached form a cyclopropyl ring;

$R^8$ is H or Me;

$R^{15}$ is H, $C_1$-$C_6$ alkyl, $C_2$-$C_6$ alkenyl, or $C_2$-$C_6$ alkynyl, wherein said alkyl, alkenyl, and alkynyl are optionally substituted with one or more groups independently selected from F, Cl, Br, I, CN, $C_1$-$C_6$ alkyl, oxo, OH, O—($C_1$-$C_6$ alkyl), S—($C_1$-$C_6$ alkyl), NH—($C_1$-$C_6$ alkyl), N—($C_1$-$C_6$ alkyl)$_2$, SO—($C_1$-$C_6$ alkyl), and $SO_2$—($C_1$-$C_6$ alkyl), or $R^{15}$ is a saturated, partially unsaturated, or fully unsaturated three to seven membered carbocyclic ring or heterocyclic ring having one or two heteroatoms independently selected from O, S and N, wherein said carbocyclic and heterocyclic rings are optionally attached to the nitrogen of the lactam ring through a $C_1$-$C_4$ alkyl, and wherein said carbocyclic and heterocyclic rings are optionally substituted with one or more groups independently selected from F, Cl, Br, I, OH, $C_1$-$C_6$ alkyl, $C_2$-$C_6$ alkenyl, $C_2$-$C_6$ alkynyl, O—($C_1$-$C_6$ alkyl), S—($C_1$-$C_6$ alkyl), $NH_2$, oxo, nitro, cyano, C(=O)OH, C(=O)O—($C_1$-$C_6$ alkyl), NH—($C_1$-$C_6$ alkyl) and N—($C_1$-$C_6$ alkyl)$_2$;

$R^{16}$, $R^{17}$ and $R^{18}$ are independently H, $C_1$-$C_6$ alkyl, $C_2$-$C_6$ alkenyl, $C_2$-$C_6$ alkynyl, saturated or partially unsaturated cycloalkyl, saturated or partially unsaturated heterocyclyl, aryl, or heteroaryl, wherein said alkyl, alkenyl, alkynyl, cycloalkyl, heterocyclyl, aryl and heteroaryl are optionally substituted with one or more groups independently selected from F, Cl, Br, I, CN, =6, =$NOR^{21}$, $NR^{21}R^{22}$, $NR^{21}$(C=O) $R^{22}$, $NR^{21}$C(=O)$NR^2R^3$, $CR^{22}$=$NOR^{21}SO_2R^{24}$, $SOR^{22}$, $SR^{22}$, $SO_2NR^{21}R^{22}$, $OR^{21}$, (C=O)$R^{21}$, (C=O)$OR^{21}$, O—(C=O)$R^{21}$, $C_1$-$C_6$ alkyl, $C_2$-$C_6$ alkenyl, $C_2$-$C_6$ alkynyl, saturated and partially unsaturated cycloalkyl, saturated and partially unsaturated heterocyclyl, and a 5- or 6-membered heteroaryl or aryl ring, or $R^{16}$ and $R^{17}$ together with the atoms to which they are attached form a saturated or partially unsaturated 5-6 membered heterocyclic ring having one or more heteroatoms independently selected from N, O and S, wherein said heterocyclic ring is optionally substituted with one or more groups independently selected from F, Cl, Br, I, CN, O, =$NOR^{21}$, $NR^{21}R^{22}$, $NR^{21}$(C=O)$R^{22}$, $NR^{21}$C(=O)$NR^{22}R^{23}$, $CR^{22}$=$NOR^{21}SO_2R^{24}$, $SOR^{22}$, $SR^{22}$, $SO_2NR^{21}R^{22}$, $OR^{21}$, (C=O)$R^{21}$, (C=O)$OR^{21}$, O—(C=O)$R^{21}$, $C_1$-$C_6$ alkyl, $C_2$-$C_6$ alkenyl, $C_2$-$C_6$ alkynyl, saturated and partially unsaturated cycloalkyl, saturated and partially unsaturated heterocyclyl, and a 5- or 6-membered heteroaryl or aryl ring, or $R^{17}$ and $R^{18}$ together with the atoms to which they are attached form a saturated or partially unsaturated 5-6 membered heterocyclic ring having one or more heteroatoms independently selected from N, O and S, wherein said heterocyclic ring is optionally substituted with one or more groups independently selected from F, Cl, Br, I, CN, =O, =$NOR^{21}$, $NR^{21}R^{22}$, $NR^{21}$(C=O)$R^{22}$, $NR^{21}$C(=O) $NR^{22}R^{23}CR^{22}$=$NOR^{21}SO_2R^{23}$, $SOR^{23}$, $SR^{22}$, $SO_2NR^{21}R^{22}$, $OR^{21}$, (C=O)$R^{21}$, (C=O)$OR^{21}$, O—(C=O) $R^{21}$, $C_1$-$C_6$ alkyl, $C_2$-$C_6$ alkenyl, $C_2$-$C_6$ alkynyl, saturated or partially unsaturated cycloalkyl, saturated or partially unsaturated heterocyclyl, and a 5-6 membered heteroaryl or aryl ring;

$R^{19}$ is $C_1$-$C_6$ alkyl, $C_2$-$C_6$ alkenyl, $C_2$-$C_6$ alkynyl, saturated or partially unsaturated $C_3$-$C_6$ cycloalkyl, saturated or partially unsaturated $C_1$-$C_6$ heterocyclyl, or a 5-6 membered heteroaryl or aryl ring, wherein said alkyl, alkenyl, alkynyl, cycloalkyl, heterocyclyl, aryl and heteroaryl are optionally substituted with one or more groups independently selected from F, Cl, Br, I, CN, =O=$NOR^{21}$, $NR^{21}R^{22}$, $NR^{21}$(C=O)

$R^{22}$, $NR^{21}C(=O)NR^{22}R^{23}$, $CR^{22}=NOR^{21}SO_2R^{23}$, $SOR^{23}$, $SR^{22}$, $SO_2NR^{21}R^{22}$, $OR^{21}$, $(C=O)R^{21}$, $(C=O)OR^{21}$, $O-(C=O)R^{21}$, $C_1$-$C_6$ alkyl, $C_2$-$C_6$ alkenyl, $C_2$-$C_6$ alkynyl, saturated or partially unsaturated $C_3$-$C_6$ cycloalkyl, saturated or partially unsaturated $C_1$-$C_6$ heterocyclyl, and a 5-6 membered heteroaryl or aryl ring;

$R^{21}$, $R^{22}$ and $R^{23}$ are independently H, $C_1$-$C_6$ alkyl, $C_2$-$C_6$ alkenyl, or $C_2$-$C_6$ alkynyl, wherein said alkyl, alkenyl, and alkynyl are optionally substituted with one or more groups independently selected from F, Cl, Br and I;

$R^{24}$ is $C_1$-$C_6$ alkyl, $C_2$-$C_6$ alkenyl, or $C_2$-$C_6$ alkynyl, wherein said alkyl, alkenyl, and alkynyl are optionally substituted with one or more groups independently selected from F, Cl, Br, and I; and each $R^{30}$ is independently F, $C_1$-$C_6$ alkyl, $C_2$-$C_6$ alkenyl, $C_2$-$C_6$ alkynyl, a saturated or partially unsaturated 3-6 membered carbocyclic ring, a 6 membered aryl ring, or a 5-6 membered heterocyclic ring having one or two heteroatoms independently selected from O, S and N, wherein said carbocyclic, aryl, and heterocyclic rings are optionally attached to the lactam ring through a $C_1$-$C_4$ alkyl, and wherein said alkyl, alkenyl, alkynyl, carbocyclic ring, aryl ring, and heterocyclic ring are optionally substituted with one or more groups independently selected from oxo, OH, SH, $NH_2$, F, Cl, Br, I, CN, $C_1$-$C_6$ alkyl, $C_2$-$C_6$ alkenyl, O—($C_1$-$C_6$ alkyl), S—($C_1$-$C_6$ alkyl), NH—($C_1$-$C_6$ alkyl), SO—($C_1$-$C_6$ alkyl), and $SO_2$—($C_1$-$C_6$ alkyl), $C(=O)OH$, and $C(=O)O$—($C_1$-$C_6$)alkyl, or two adjacent $R^{30}$ groups together with the atoms to which they are attached form a 6 membered saturated or partially unsaturated carbocyclic ring or a 6 membered aryl ring.

An example of a value for B is H.
An example of a value for X is O.
In certain embodiments of Formula I, X is O and B is H.
An example of a value for $R^8$ is H.
In certain embodiments, each $R^{30}$ is independently selected from any of the values described above, other than F.
In one embodiment, the compounds may be represented by the formula

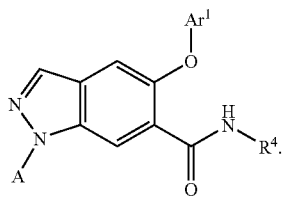

In certain embodiments, $Ar^1$ is optionally substituted aryl. For example, in certain embodiments $Ar^1$ is phenyl optionally substituted with one or more groups independently selected from F, Cl, Br, I, $OR^{16}$, or $C_1$-$C_6$ alkyl, wherein said alkyl is optionally substituted with one or more groups independently selected from F, C, Br and I. In certain embodiments, $Ar^1$ is phenyl substituted with one or more F. An exemplary embodiment of $Ar^1$ is 2,4-difluorophenyl.

In certain embodiments, A is optionally substituted $C_1$-$C_6$ alkyl. For example, in certain embodiments A is $C_1$-$C_6$ alkyl optionally substituted with one or more groups independently selected from F, Cl, Br, I and $OR^6$. In certain embodiments, A is $C_1$-$C_6$ alkyl substituted with one or more groups independently selected from OH and F.

Exemplary embodiments of A include, but are not limited to,

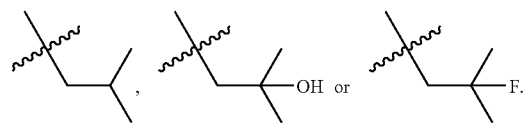

Exemplary embodiments of $R^4$ include the structures (i)-(v):

(i)

(ii)

(iii)

(iv)

(v)

wherein structures (i), (ii), and (iii) are optionally substituted with one to four $R^{30}$ groups, and structures (iv) and (v) are optionally substituted with one to three $R^{30}$ groups. In certain embodiments, the $R^4$ group is substituted with two adjacent $R^{30}$ groups, wherein the $R^{30}$ groups together with the ring carbons atoms to which they are attached form a 6 membered saturated or partially unsaturated carbocyclic ring or a 6 membered aryl ring. Exemplary embodiments include, but are not limited to:

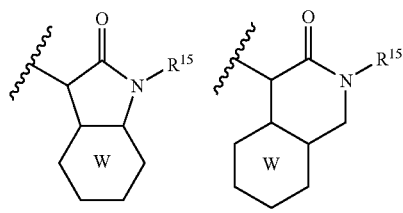

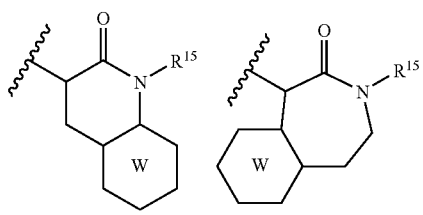
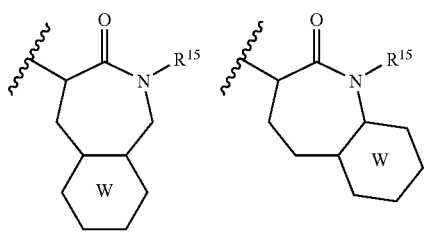

wherein ring W is a saturated, partially unsaturated or fully unsaturated ring. In other embodiments, R⁴ is unsubstituted.

In certain embodiments, G is —CH₂CH₂—, —CH₂CH₂CH₂— or —CH₂CH₂CH₂CH₂—.

In certain embodiments, the ring in R⁴ is saturated (i.e. G is a $C_2$-$C_4$ alkylene chain) and the lactam ring carbon alpha to the carbonyl is in the (S) configuration:

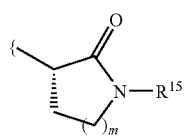

where m is 1 to 3

Exemplary embodiments of compounds of Formula I include, but are not limited to, compounds selected from the formulas:

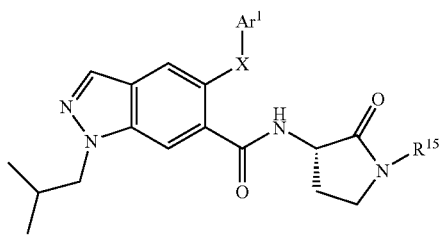

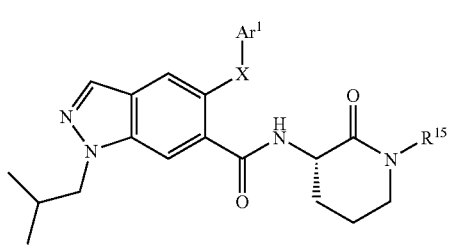

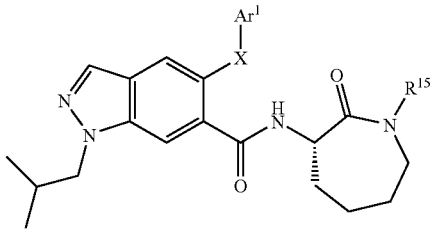

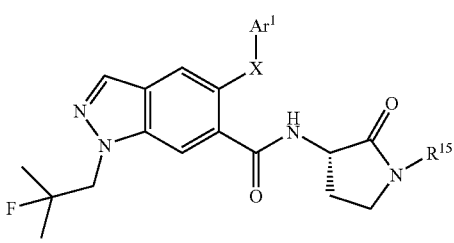

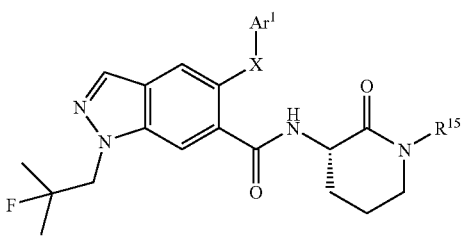

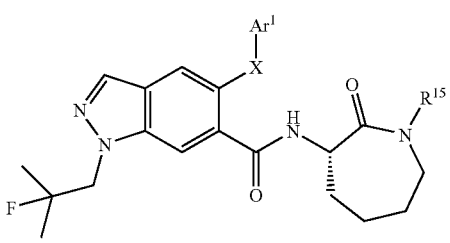

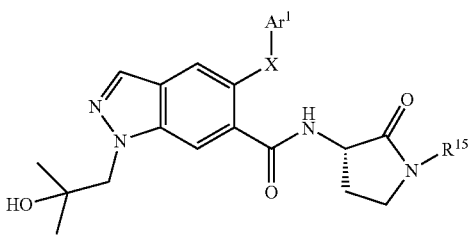

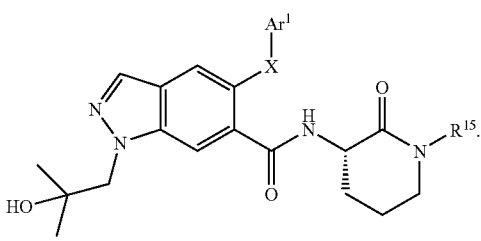

wherein $Ar^1$ and $R^{15}$ are as defined above.

Exemplary embodiments of compounds of Formula I further include, but are not limited to, compounds selected from the formulas:

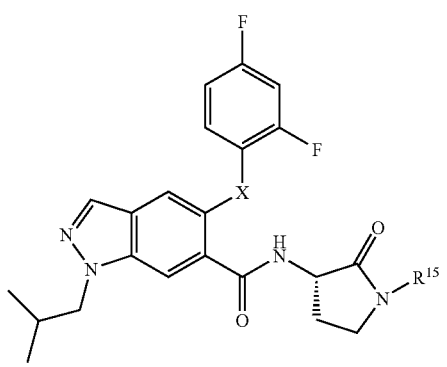
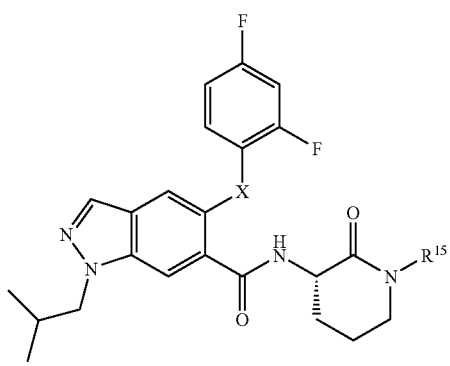
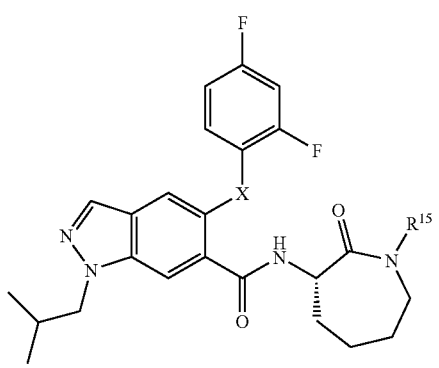
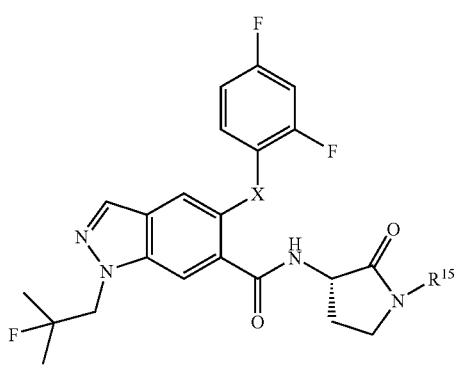
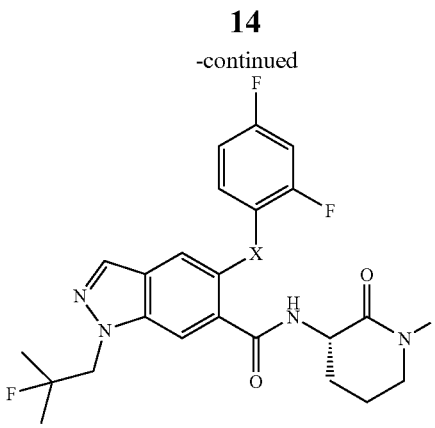
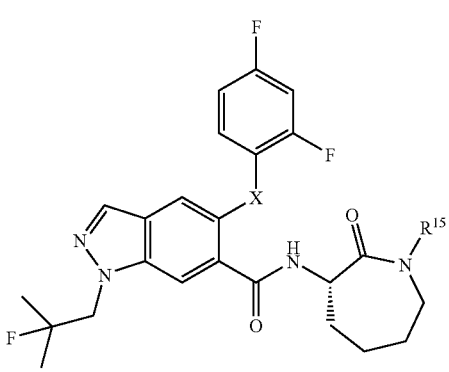
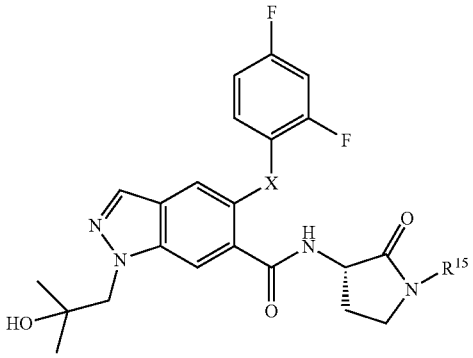
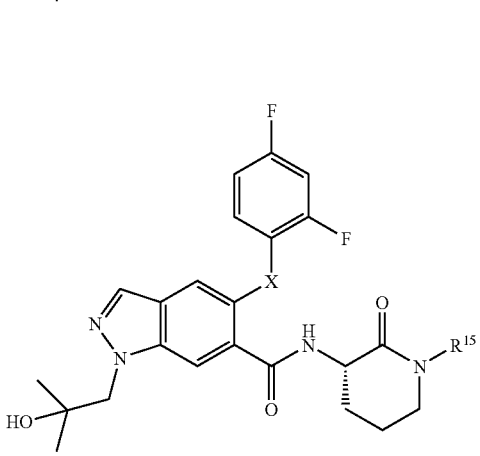
wherein R[15] is as defined above.
Exemplary embodiments of compounds of Formula I further include, but are not limited to, compounds selected from the formulas:

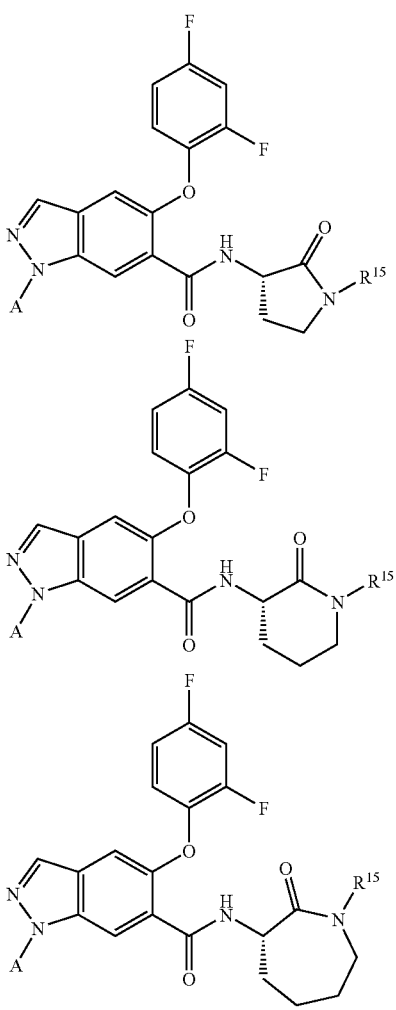

wherein A and are as defined above. In certain embodiments, A is optionally substituted $C_1$-$C_{12}$ alkyl. For example, in certain embodiments A is $C_1$-$C_6$ alkyl optionally substituted with one or more groups independently selected from $OR^{16}$, F, Cl, Br and I. In certain embodiments, A is

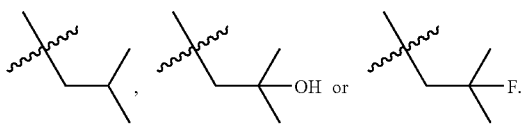

In certain embodiments, $R^{15}$ is H or optionally substituted $C_1$-$C_6$ alkyl. For example, in certain embodiments R's is H, methyl or $CH_2CH_2OH$.

Examples of specific compounds of formula I are the compounds of Examples 16, 17, 18, 19, 20, 21, 22, 23, 24, 25, 27, 28, 29 and 30 herein, and pharmaceutically acceptable salts thereof. Particular mention may be made of the compound of Example 27. This compound has been found to have a desirable profile of properties, in particular relatively good bioavailability, relatively low first pass metabolism, low affinity for p-glycoprotein (PGP) transporter (which affects cell permeability), and low activity in the hERG channel (a predictor for cardiac side effects).

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of this invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also provides a compound of formula (I) or a salt thereof which is in isolated form (for example, in a pharmaceutically acceptable state of purity, or in crystalline form). It also provides a compound of formula (I) or a salt thereof when prepared by a synthetic chemical process.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formula I, the invention also includes solvates, prodrugs, and salts of such compounds.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "prodrug" is a compound that may be converted under physiological conditions or by solvolysis to the specified compound or to a salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of this invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of this invention can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1-C_6)$alkanoyloxymethyl, $1-((C_1-C_6)$alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

Free amine groups of compounds of this invention can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —$C(OY_0)Y_1$ wherein $Y_0$ is $(C_1-C_4)$ alkyl and $Y_1$ is $(C_1-C_6)$alkyl, carboxy $(C_1-C_6)$alkyl, amino$(C_1-C_4)$alkyl or mono-N- or di-N,N-$(C_1-C_6)$alkylaminoalkyl, or —$C(Y_2)Y_3$ wherein $Y_2$ is H or methyl and $Y_3$ is mono-N- or di-N,N-$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (*Academic Press, 1985*); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

A compound of the invention may possess a sufficiently acidic group, a sufficiently basic group, or both functional groups, and accordingly react with any of a number of inorganic or organic bases or acids to form a salt. Examples of salts include those salts prepared by reaction of the compounds of this invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, bxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates; phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of this invention may include more than one acidic or basic moiety, the compounds of this invention may include mono, di or tri-salts in a single compound.

If the inventive compound is a base, the desired salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

This invention further includes pharmaceutically acceptable salts and prodrugs of the compounds of Formula I. The phrase "pharmaceutically acceptable" indicates that the substance or composition is compatible chemically and/or toxicologically with the other ingredients comprising a formulation, and/or the mammal being treated therewith.

A "pharmaceutically acceptable salt," unless otherwise indicated, refers to a salt that retains the biological effectiveness of the corresponding free acid or base of the specified compound and is not biologically or otherwise undesirable.

This invention also embraces isotopically-labeled compounds of this invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of this invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of this invention can generally be prepared by following procedures analogous to those disclosed in the Schemes and/or in the Examples herein below, by substituting an isotopically labeled reagent for a non-isotopically labeled reagent.

Metabolites

Also falling within the scope of this invention are in vivo metabolites of compounds of this invention. A "metabolite" is a pharmacologically active product produced through metabolism in the body of a specified compound or salt thereof. Such products may result, for example, from the oxidation, reduction, hydrolysis, amidation, deamidation, esterification, deesterification, enzymatic cleavage, and the like; of the administered compound. Accordingly, the invention includes metabolites of a compound of this invention, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Synthesis of Compounds of the Invention

The compounds of this invention may be prepared by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

The compounds of this invention may be prepared singly or as compound libraries comprising at least 2, for example 5 to 1,000 compounds, or 10 to 100 compounds. Libraries of compounds of this invention may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-8 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

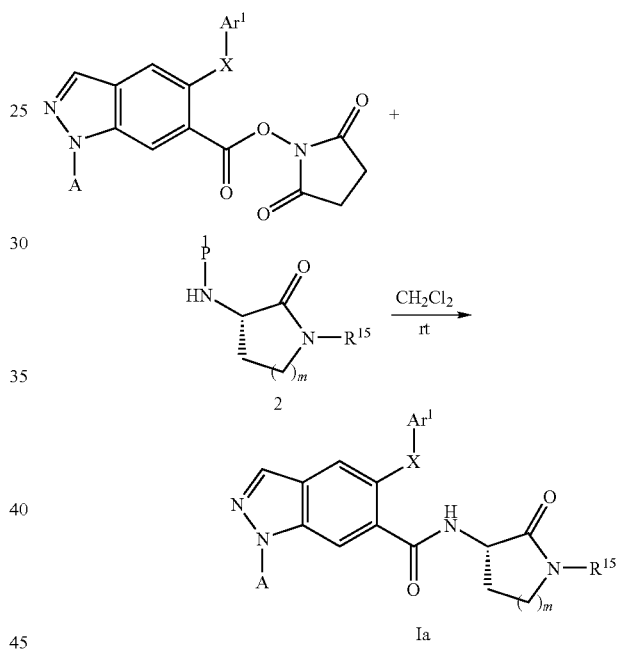

Scheme 1 shows a general method of preparing compounds of Formula Ia wherein $X, A, R^{15}, Ar^1$ are as defined herein and m is 1, 2 or 3. According to Scheme 1, indazole (1) (prepared, for example, as shown in Scheme 3) is coupled with a protected or unprotected lactam (2), where P is hydrogen or an amine protecting group, in an organic solvent such as $CH_2Cl_2$, to provide compound (1).

Scheme 2

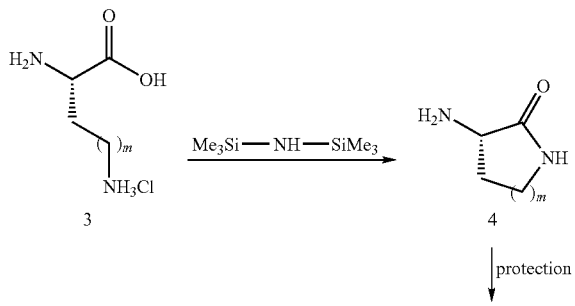

protection

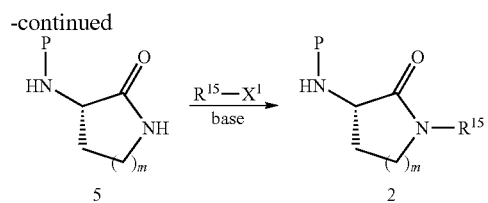

Scheme 2 shows a method of preparing lactam intermediates (4) and (2) suitable for use in the coupling reaction shown in Scheme 1, wherein R$^{15}$ and p are as defined herein, P is an amine protecting group and m is 1, 2 or 3. According to Scheme 2, amino acid (3) is cyclized upon treatment with, for example bis-trimethylsilylamine or HCl in methanol, to provide the lactam (4) wherein P is hydrogen. The primary amino group of lactam (4) can be protected under standard conditions to provide the protected amino lactam (5) wherein P is an amine protecting group. Suitable reagents for protecting the amino group include, but are not limited to, di-t-butyl dicarbonate. The protected amino lactam (5) can be alkylated with R$^{15}$—X$^1$, wherein X$^1$ is Br, in the presence of a base, such as NaH, in a suitable organic solvent such as THF, DMF, or a mixture of THF and DMF to provide the alkylated lactam (2).

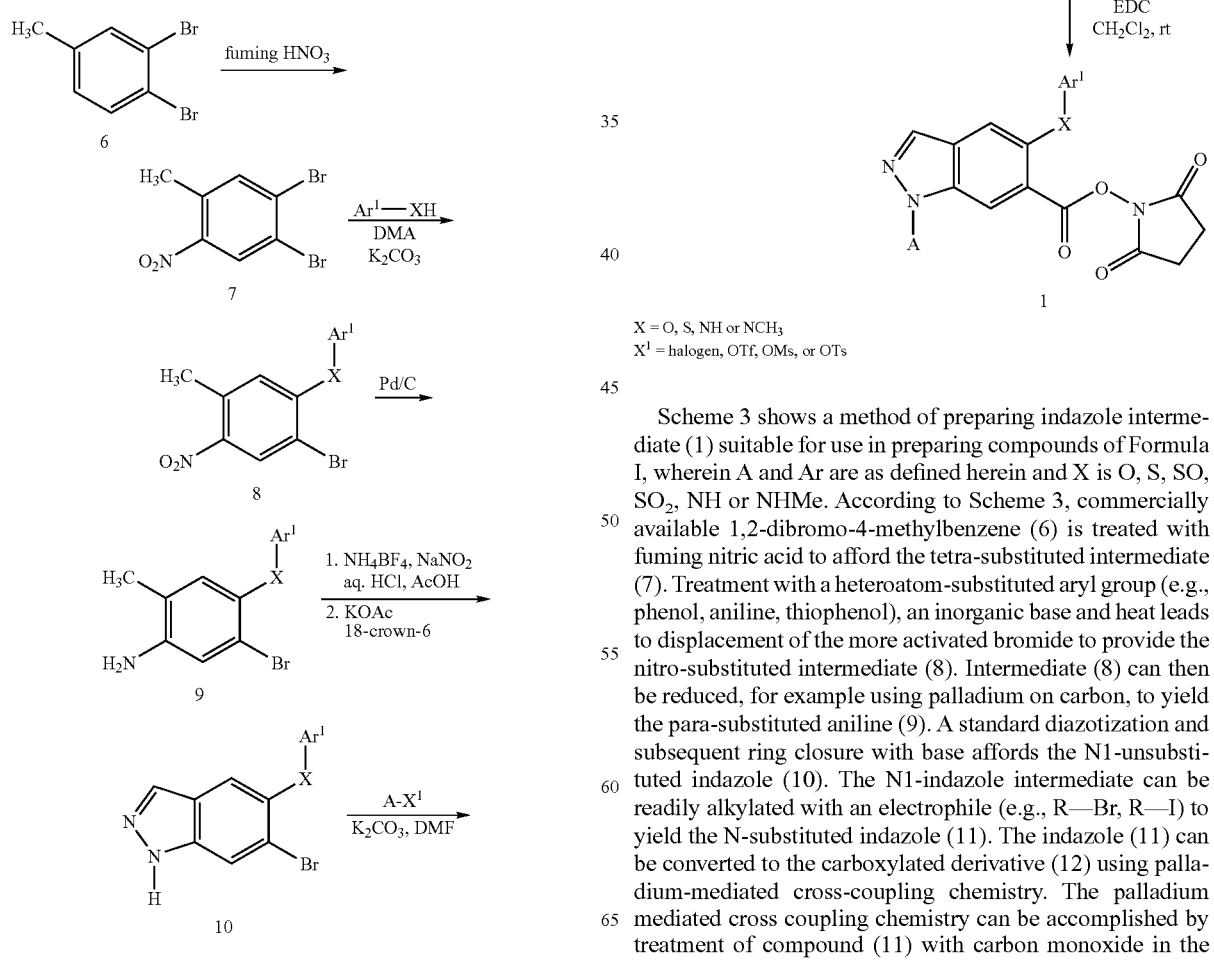

X = O, S, NH or NCH$_3$
X$^1$ = halogen, OTf, OMs, or OTs

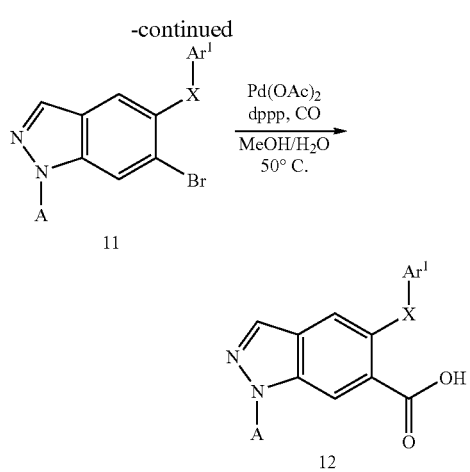

Scheme 3 shows a method of preparing indazole intermediate (1) suitable for use in preparing compounds of Formula I, wherein A and Ar are as defined herein and X is O, S, SO, SO$_2$, NH or NHMe. According to Scheme 3, commercially available 1,2-dibromo-4-methylbenzene (6) is treated with fuming nitric acid to afford the tetra-substituted intermediate (7). Treatment with a heteroatom-substituted aryl group (e.g., phenol, aniline, thiophenol), an inorganic base and heat leads to displacement of the more activated bromide to provide the nitro-substituted intermediate (8). Intermediate (8) can then be reduced, for example using palladium on carbon, to yield the para-substituted aniline (9). A standard diazotization and subsequent ring closure with base affords the N1-unsubstituted indazole (10). The N1-indazole intermediate can be readily alkylated with an electrophile (e.g., R—Br, R—I) to yield the N-substituted indazole (11). The indazole (11) can be converted to the carboxylated derivative (12) using palladium-mediated cross-coupling chemistry. The palladium mediated cross coupling chemistry can be accomplished by treatment of compound (11) with carbon monoxide in the presence of a suitable catalyst such as Pd(OAc)$_2$ in a suitable solvent system such as MeOH/H$_2$O at elevated temperatures. If X=S, the compounds can be carried forward as the sulfide, or the sulfur can be oxidized to the sulfone or sulfoxide with a mild oxidizing agent before the subsequent activation step. Compound (12) is then treated with N-hydroxysuccinimide in the presence of a coupling agent such as 1-(3-dimethylaminopropyl)-3-ethylcarbodiimide hydrochloride (EDC) to provide compound (1). If the A group contains a functional group, it can be further modified if desired. For example, a hydroxyl group can be replaced with a fluorine group using methods known to those skilled in the art.

Scheme 4

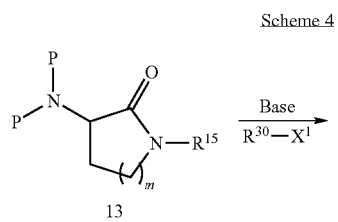

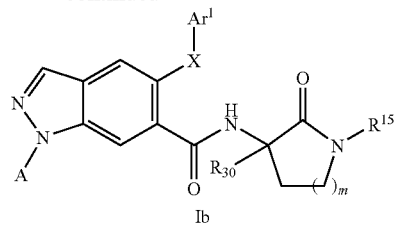

Scheme 4 shows a method of functionalizing a suitably protected alpha-amino lactam in the alpha position to provide a compound of Formula Ib, wherein X, A, Ar$^1$, R$^{15}$ and R$^{30}$ are as defined herein, and m is 1, 2 or 3. According to Scheme 4, treatment of a protected alpha-amino lactam (13) with a strong base followed by quenching of the resulting anion with a suitable electrophile that incorporates the desired R$^{30}$ group provides the substituted lactam (14). Subsequent deprotection provides the free amine (15), which can be coupled with a heterocyclic acid via a variety of amide coupling conditions according to the methods described herein to provide a compound of Formula Ib.

Scheme 5

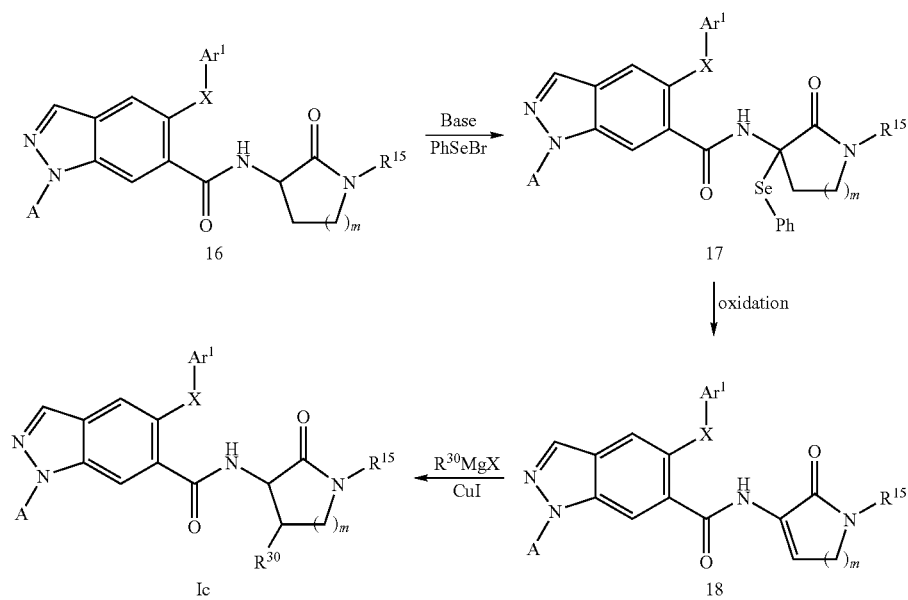

-continued

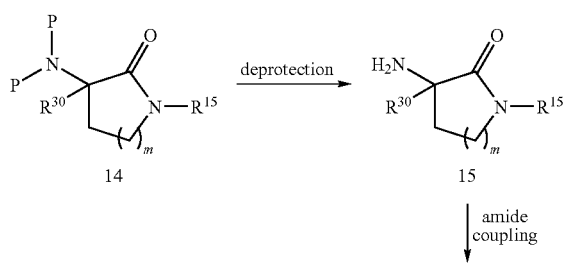

Scheme 5 shows a method of introducing a side chain at the beta position of an amino-lactam to provide a compound of Formula Ic, wherein X, A, Ar$^1$, and R$^{15}$ are as defined herein, and m is 1, 2, or 3. According to Scheme 5, lactam (16) can be converted to the alpha-beta unsaturated lactam (17) via selenation using a strong base and phenyl selenyl halide as an electrophile followed by oxidation of the intermediate selenide and beta elimination to provide lactam (18). The resulting unsaturated lactam (18) can then be treated with a nucleophile, such as R$^{30}$MgX in the presence of CuI, to introduce an R$^{30}$ group at the beta position to provide a compound of Formula Ic.

Scheme 6

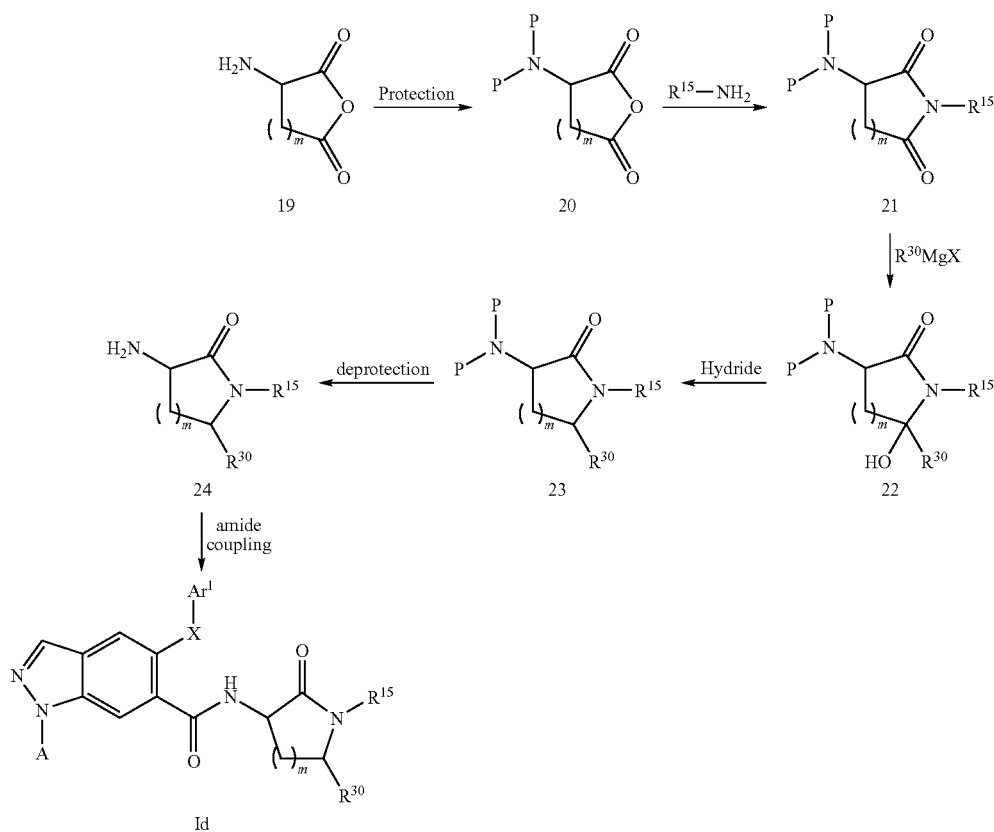

Scheme 6 shows a method of generating an $R^{30}$ substitution alpha to the ring nitrogen of a lactam to provide a compound of Formula Id, wherein X, A, $Ar^1$, $R^{15}$ and $R^{30}$ are as defined herein, and m is 1, 2 or 3. According to Scheme 6, the nitrogen atom of the commercially available alpha amino cyclic anhydride (19) can be reacted with a suitable protecting group to provide compound (20). Conversion of the protected anhydride (20) to the imide in one (or several) steps by treatment with a compound of the formula $R^{15}NH_2$ provides an intermediate amide-acid closes to the imide on heating or under dehydrative conditions to provide imide (21). The imide (21) can then be treated with a suitable nucleophile, such as $R^{30}MgX$, which will react with the distal, less sterically hindered carbonyl carbon to provide a substituted hemi-ketal (22). The hemi-ketal (22) can be further reduced by treatment with a suitable hydride reducing agent to provide the functionalized lactam (23). Subsequent deprotection of the alpha amino group of compound (23) to provide compound (24), followed by coupling of (24) to a heterocyclic acid under standard amide coupling conditions such as described herein provides the substituted compound of Formula Id.

Scheme 7

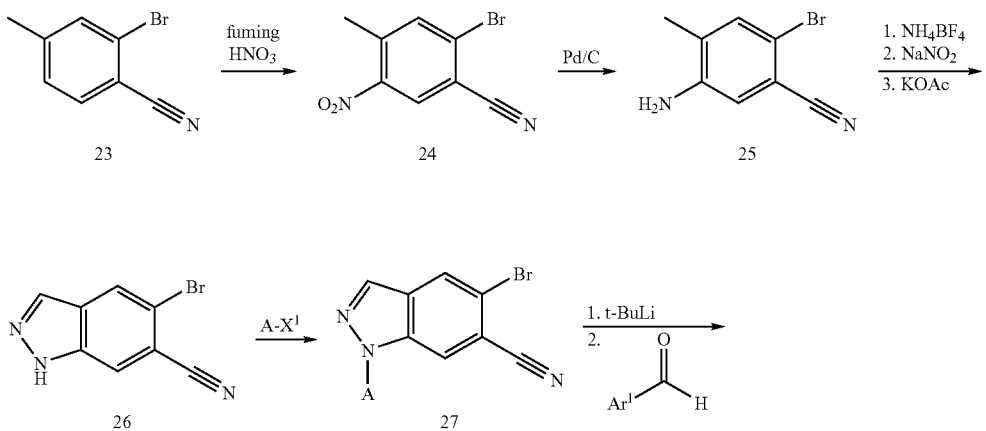

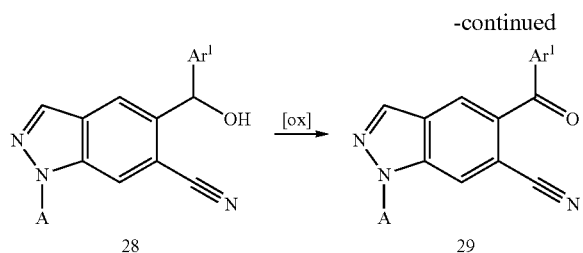
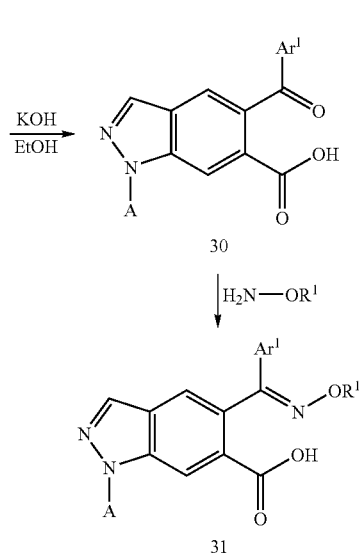
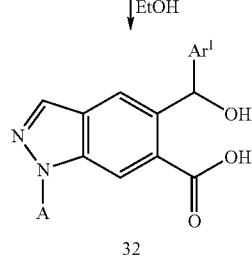

Scheme 7 shows a method of preparing intermediates (30), (31) and (32) wherein X is C=O, C=NOR¹, or CHOR¹, respectively, and A and Ar¹ are as defined herein, which can be used to make compounds of Formula I. According to Scheme 7, commercially available 2-bromo-4-methylbenzonitrile (23) is treated with fuming nitric acid to afford the tetra-substituted intermediate (24). Intermediate (24) is then treated with palladium on carbon to reduce the nitro group (25) to NH₂. Subjecting compound (25) to diazotization conditions, followed by ring closure with base to afford the N1-unsubstituted indazole (26). The N1-indazole can be readily alkylated with an electrophile A-X¹ to yield (27). Metal-halogen exchange followed by quenching with an electrophilic aldehyde yields intermediate alcohol (28). The alcohol (28) can be oxidized to the ketone using, for example standard Dess-Martin conditions, to produce the nitrile (29). Hydrolysis of the nitrile (29) in aqueous base affords intermediate (30). Alternatively, the nitrile group of compound (28) can be hydrolyzed in aqueous base to form the intermediate (31). Any of compounds (30), (31) and (32) can subsequently be coupled to a heterocyclic acid under standard amide coupling conditions such as described herein to provide a compound of Formula Ia.

Scheme 8

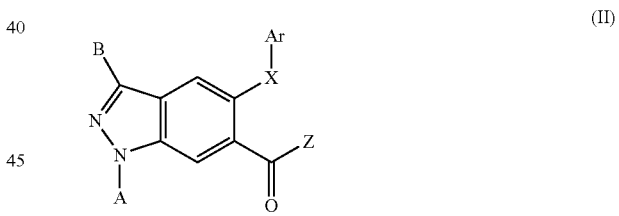
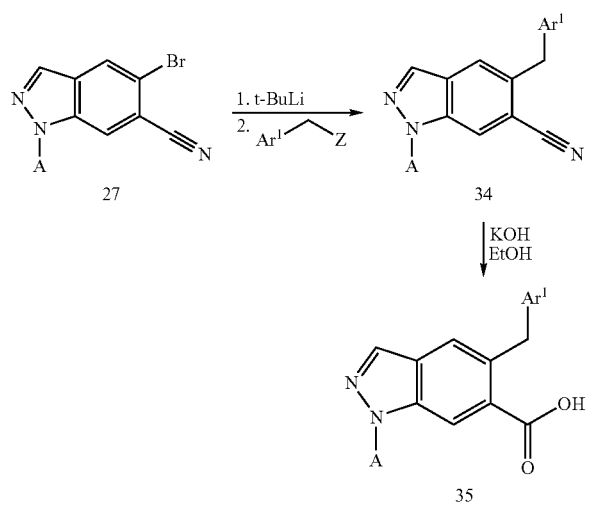

Scheme 8 shows a method of preparing intermediate (35) wherein X is CH₂, and A and Ar¹ are as defined herein, which can be used to prepare compounds of Formula Ia. According to Scheme 8, intermediate (27), prepared as described in Scheme 7, is treated with t-butyl lithium, for example in a metal-halogen exchange reaction, followed by quenching with an electrophilic benzyl group, such as benzyl bromide, to provide compound (34), which is then hydrolyzed to provide the acid (35).

According to another aspect, therefore, the present invention provides a method of preparing a compound of formula I, or a salt thereof, which comprises coupling a compound having the formula (II)

(II)

in which Z represents OH or a leaving atom or group, with a compound having the formula (III)

HNR$^{8a}$R$^{4}$ (III)

wherein R$^{8a}$ is R$^{8}$ or an amine protecting group;

followed by removing any amine protecting group and, if desired, forming a salt.

The method may be performed using standard amide bond forming conditions well known in the art. The leaving atom or group may be, for example, a halogen atom (such as a chlorine atom, an alkoxy group (such as (1-6C)alkoxy), or an organoaminooxy group (such as 2,5-dioxopyrrolidin-1-yloxy), or formed in situ using a coupling agent such as 1-(3-dimethylaminopropyl)-3-ethylcarbodiimide hydrochloride (EDC).

In one embodiment, the method comprises coupling a compound having the formula

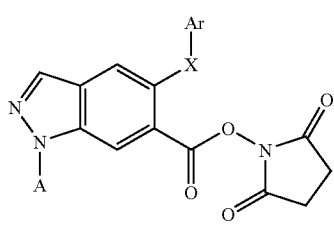

with a compound having the formula

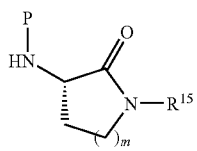

wherein P is H or an amine protecting group and m is 1, 2 or 3, and if necessary removing said protecting group.

In preparing compounds of this invention, protection of remote functionalities (e.g., primary or secondary amines, alcohols, etc.) of intermediates may be necessary. The need for such protection will vary depending on the nature of the remote functionality and the conditions of the preparation methods. For example, suitable amino-protecting groups (NH—P) include acetyl, trifluoroacetyl, t-butoxycarbonyl (BOC), benzyloxycarbonyl (CBz) and 9-fluorenylmethyl-eneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of this invention, it may be advantageous to separate reaction products from one another and/or from starting materials. The desired products of each step or series of steps is separated and/or purified to the desired degree of homogeneity by the techniques common in the art. Such separations involve, for example, multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by-product, or the like. Such reagents include adsorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate method(s) of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of this invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513: 375-378). Enriched or purified enantiomers can be distinguished by methods used to distinguish other chiral molecules with asymmetric carbon atoms, such as optical rotation and circular dichroism.

Methods of Treatment

The compounds of the invention may be used to treat diseases mediated by modulation or regulation of protein kinases. Accordingly, another aspect of the invention provides methods of treating or preventing diseases or conditions described herein by administering to a mammal, such as a human, a therapeutically effective amount of a compound of this invention in an amount effective to treat or prevent said disorder. In one embodiment, the method comprises administering to a mammal a compound of this invention in an amount effective to inhibit one or more kinases such as p38 MAPK.

An "effective amount" refers to an amount of compound that, when administered to a mammal in need of such treatment, is sufficient to effect treatment for a disease mediated by the activity of one or more protein kinases, such as p38 MAPK, and the associated kinase-mediated events such as cytokine production. Thus, for example, a therapeutically effective amount of a compound of this invention is a quantity sufficient to modulate, regulate, or inhibit the activity of one or more protein kinases such that a disease condition which is mediated by that activity is reduced or alleviated.

"Treating" is intended to mean at least the mitigation of a disease condition in a mammal, such as a human, that is affected, at least in part, by the activity of one or more protein kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The amount of a compound of this invention administered to a mammal will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

In one aspect of this invention, the compounds of this invention or pharmaceutical salts thereof may be formulated into pharmaceutical compositions for administration to animals or humans to treat or prevent a p38 kinase-mediated condition. The term "p38 kinase-mediated condition" as used herein means any disease or other deleterious condition in which p38 is known to play a role, and includes conditions that are known to be caused by IL-1, TNF, IL-6 or IL-8 overproduction. Such conditions include, but are not limited to, inflammatory diseases, respiratory diseases, autoimmune diseases, destructive bone disorders, proliferative disorders, infectious diseases, viral disease, fibrotic disease and neurodegenerative diseases.

Inflammatory diseases which may be treated or prevented include, but are not limited to, acute pancreatitis, chronic pancreatitis, asthma, allergies, cystic fibrosis, idiopathic pulmonary fibrosis, idiopathic pneumonias, interstitial lung diseases, chronic obstructive pulmonary disease, allergic rhinitis, emphysema, bronchitis and adult respiratory distress syndrome.

Respiratory diseases and disorders which may be treated or prevented include, but are not limited to, airway inflammation, chronic obstructive pulmonary disease (COPD), asthma, allergic and non-allergic rhinitis, cystic fibrosis (CF), idiopathic pulmonary fibrosis (IPF), interstitial lung disease, adult respiratory distress syndrome (ARDS), and other cytokine mediated diseases of the airway and pulmonary system.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Fibrotic diseases which may be treated or prevented include, but are not limited to, idiopathic pulmonary fibrosis, kidney and liver fibrosis.

Proliferative diseases which may be treated or prevented include, but are not limited to, acute myelogenous leukemia, chronic myelogenous leukemia, metastatic melanoma, Kaposi's sarcoma, myelodysplastic syndrome, multiple myeloma, astrocytoma, bone cancer, brain cancer, breast cancer, colorectal cancer, gastric cancer, glioma, glioblastoma, multiforme, head and neck cancer, hematological cancer, hematopoiesis disorders, interstitial lung diseases, kaposi's sarcoma, lymphocytic leukemia, melanoma, myeloid leukemia, non-small cell lung cancer, ovarian cancer, prostate cancer, sarcoma, skin cancer, small cell lung cancer, and stomach cancer. Other patients which can be treated include those undergoing bone marrow transplantation.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Degenerative conditions or diseases which may be treated or prevented by the compounds of this invention include, but are not limited to, Alzheimer's disease, Parkinson's disease, cerebral ischemia and other neurodegenerative diseases.

The term "p38-mediated conditions" also includes ischemia/reperfusion in stroke, heart attacks, myocardial ischemia, organ hypoxia, vascular hyperplasia, cardiac hypertrophy and thrombin-induced platelet aggregation.

In addition, the compounds of this invention are also useful for inhibiting the expression of inducible pro-inflammatory proteins such as prostaglandin endoperoxide synthase-2 (PGHS-2), also referred to as cyclooxygenase-2 (COX-2). Therefore, other "p38 kinase-mediated conditions" include, but are not limited to, edema, analgesia, fever and pain, such as neuromuscular pain, headache, cancer pain, dental pain and arthritis pain.

The conditions and diseases that may be treated or prevented by the compounds of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated diseases or conditions include, but are not limited to, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections such as HIV, CMV, influenza and herpes; and veterinary viral infections such as lentivirus infections (e.g., equine infectious anaemia virus, caprine arthritis virus, visna virus or maedi virus); and retrovirus infections (e.g., feline immunodeficiency virus, bovine immunodeficiency virus, or canine immunodeficiency virus).

IL-8 mediated diseases or conditions include, but are not limited to, diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat or prevent conditions caused or exacerbated by IL-1 or TNF. Such conditions include, but are not limited to, inflamed joints, eczema, psoriasis, inflammatory skin conditions such as sunburn, inflammatory eye conditions such as conjunctivitis, pyresis, pain and other conditions associated with inflammation.

Although the compounds of this invention are primarily of value as therapeutic agents for use in warm-blooded animals (including humans), they are also useful whenever it is required to inhibit the effects of cytokines. Thus, they are useful as pharmacological standards for use in the development of new biological tests and in the search for new pharmacological agents.

The size of the dose for therapeutic or prophylactic purposes of a compound of this invention will naturally vary according to the nature and severity of the conditions, the age and sex of the animal or patient and the route of administration, according to well known principles of medicine.

This invention further provides compounds of this invention for use in therapy. An additional aspect of the invention is the use of a compound of this invention in the preparation of a medicament for use as a p38 kinase inhibitor.

Combination Therapy

The compounds of this invention may be used in combination with other drugs and therapies used in the treatment of disease states which would benefit from the inhibition of kinases and the associated cytokines such as IL-1, TNF, IL-6 or IL-8. The dose of the second drug can be appropriately selected based on a clinically employed dose. The proportion of the compound of this invention and the second drug can be appropriately determined according to the administration subject, the administration route, the target disease, the clinical condition, the combination, and other factors. In cases where the administration subject is a human, for instance, the second drug may be used, for example, in an amount of 0.01 to 100 parts by weight per part by weight of the compound of this invention. Larger or smaller doses may be administered to achieve the desired effect.

The second drug of the pharmaceutical combination formulation or dosing regimen has, for example, complementary activities to the compound of this invention such that they do not adversely affect each other. Such drugs are suitably present in combination in amounts that are effective for the purpose intended. Accordingly, another aspect of this invention provides a composition comprising a compound of this invention in combination with a second drug, such as described herein.

The compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when a compound of this invention and the second drug are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when a compound of this invention and the second drug are administered or delivered sequentially, e.g., by different injections in separate syringes. For example, during alternation therapy, an effective dosage of each active ingredient can be administered sequentially, i.e., serially, whereas in combination therapy, effective dosages of two or more active ingredients are administered together.

For example, by virtue of their ability to inhibit cytokines, the compounds of this invention are of value in the treatment of certain inflammatory and non-inflammatory diseases which are currently treated with a cyclooxygenase-inhibitory non-steroidal anti-inflammatory drug (NSAID) such as indomethacin ketorolac, acetylsalicylic acid, ibuprofen, sulindac, tolmetin and piroxicam. Co-administration of a compound of this invention with a NSAID can result in a reduction of the quantity of the latter agent needed to produce a therapeutic effect, and thus the likelihood of adverse side-effects from the NSAID such as gastrointestinal effects are reduced. Thus according to a further feature of the invention there is provided a pharmaceutical composition which comprises a compound of this invention, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of this invention may also be used in the treatment of conditions such as rheumatoid arthritis in combination with anti-arthritic agents such as gold, methotrexate, steroids and pencillinamine, and in conditions such as osteoarthritis in combination with steroids.

The compounds of this invention may also be used in the treatment of degradative diseases, for example osteoarthritis, in combination with chondroprotective, anti-degradative and/or reparative agents such as Diacerhein, hyaluronic acid formulations such as Hyalan, Rumalon, Arteparon and glucosamine salts such as Antril.

The compounds of this invention may also be used in the treatment of asthma in combination with anti-asthmatic agents such as bronchodilators and leukotriene antagonists.

Administration of Compounds of the Invention

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the route used may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Compositions

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of this invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical compositions of this invention may be prepared for various routes and types of administration. For example, a compound of this invention having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range for example from about 3 to about 8. Formulation in an acetate buffer at pH 5 is a suitable embodiment. The formulations may be prepared using conventional dissolution and mixing procedures. For example, the bulk drug substance (i.e.; compound of this invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of this invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of this invention or pharmaceutical composition thereof) or aid in the manufacturing of the pharmaceutical product (i.e., medicament). Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

Sustained-release preparations of compounds of this invention may be prepared. Suitable examples of sustained-release preparations include semipermeable matrices of solid hydrophobic polymers containing a compound of this invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(–)-3-hydroxybutyric acid.

The pharmaceutical compositions of this invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Pharmaceutical compositions of this invention suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be formulated in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions comprising a compound of this invention that are formulated for inhalation or intrapulmonary delivery to a mammal may be in the form of an inhalable powder, a propellant-containing inhalable aerosol, or a propellant-free inhalable solution or suspension, such as described below.

Inhalable Powders

In certain embodiment, compositions of this invention for inhalation may be in the form of inhalable powders, which may be packed into suitable capsules (inhalettes) and administered using suitable powder inhalers. Inhalable powders according to the invention may contain a compound of this invention either on its own or in admixture with one or more suitable physiologically acceptable excipients. If the compound of this invention is present in admixture with physiologically acceptable excipient(s), the following physiologically acceptable excipients may be used to prepare these inhalable powders according to the invention: monosaccharides (e.g., glucose or arabinose), disaccharides (e.g., lactose, saccharose, maltose), oligo- and polysaccharides (e.g., dextrane), polyalcohols (e.g., sorbitol, mannitol, xylitol), salts (e.g., sodium chloride, calcium carbonate) or mixtures of these excipients with one another. As an example, mono- or disaccharides can be used.

In certain embodiments of inhalable powders according to this invention, the excipients have a maximum average particle size of up to 250 μm, for example between 10 and 150 μm, and as a further example between 15 and 80 μm. It may sometimes seem appropriate to add finer excipient fractions with an average particle size of 1 to 9 μm to the excipients mentioned above. These finer excipients may be selected from the group of possible excipients listed herein. As a further example, in order to prepare an inhalable powder according to the invention, a micronised compound of this invention, for example with an average particle size of 0.5 to 10 μm, is added to the excipient mixture. Processes for producing the inhalable powders according to the invention by grinding, and micronising and mixing the ingredients together are well known in the art.

The inhalable powders according to the invention may be administered, for example, using inhalers known in the art. Inhalable powders which contain a physiologically acceptable excipient in addition to a compound of this invention may be administered, for example, by means of inhalers which deliver a single dose from a supply using a measuring chamber such as described in U.S. Pat. No. 4,570,630, or by other means know in the art. The inhalable powders according to the invention comprising a p38 MAPKinhibitor of this invention optionally combined with a physiologically acceptable excipient may be administered for example with an inhaler as disclosed in U.S. Pat. No. 4,907,583. In certain embodiments, the inhalable powders according to the invention are packed into capsules (to produce so-called inhalettes) which are used in inhalers as described, for example, in U.S. Pat. No. 5,947,118.

Propellant-Driven Inhalable Aerosols

In certain embodiments, a compound of this invention may be in the form of an aerosol suitable for inhalation. Inhalation aerosols containing propellant gas according to the invention may contain a compound of this invention dissolved in a propellant gas or in dispersed form. Suitable propellant gases which may be used include, but are not limited to, hydrocarbons such as n-propane, n-butane or isobutene, halohydrocarbons such as fluorinated derivatives of methane, ethane, propane, butane, cyclopropane or cyclobutane (e.g., TG134a (1,1,1,2-tetrafluoroethane) and TG227 (1,1,1,2,3,3,3-heptafluoropropane), and mixtures thereof.

The propellant-driven inhalation aerosols according to the invention may also contain other ingredients such as co-solvents, stabilizers, surfactants, antioxidants, lubricants and pH adjusters.

In certain embodiments, the inhalation aerosols containing propellant gas according to the invention may contain up to 5 wt. % of a compound of this invention. For example, inhalation aerosols may contain 0.002 to 5 wt. %, 0.01 to 3 wt. %, 0.015 to 2 wt. %, 0.1 to 2 wt. %, 0.5 to 2 wt. % or 0.5 to 1.5 wt. % of a compound of the invention.

If a compound of this invention is present in dispersed form, the particles of the compound have, for example, an average particle size of up to 10 μm, as a further example from 0.1 to 5 μm, and as a further example from 1 to 5 μm.

The propellant-driven inhalation aerosols according to the invention mentioned above may be administered, for example, using inhalers known in the art such as metered dose inhalers (MDI's). Accordingly, in another aspect, the present invention relates to pharmaceutical compositions in the form of propellant-driven aerosols combined with one or more inhalers suitable for administering these aerosols.

Propellant-Free Inhalable Solutions and Suspensions

A compound of this invention may also be inhaled in the form of a propellant-free inhalable solution, nanosuspension or suspension. As used herein, the term "nanosuspension" refers to a disperse system of solid-in-liquid or solid-in-semi-solid, the dispersed phase comprising a compound of this invention alone or together with a second therapeutic agent as described herein for combination therapy. The average diameter of the dispersed phase is between 10 nm and 1,000 nm (determined by photon correlation spectroscopy), the distribution of the population being quite narrow, i.e., the proportion of microparticles in the particle population is very low. The nanosuspension can be surfactant-free, but can also comprise surfactants or stabilizers or both. The nanosuspension can also be lyophilized or spray dried, and the nanoparticles of a nanosuspension can also be incorporated into a solid carrier matrix.

The solvent used to prepare the solution or suspension may be, for example an aqueous or alcoholic (e.g., ethanol) solution. The solvent may be, for example, water on its own or a mixture of water and ethanol, wherein the relative proportion of ethanol to water is, for example, up to 70 percent by volume ethanol in water, as a further example up to 60 percent by volume ethanol in water, and as a further example up to 30 percent by volume ethanol in water. The solution or suspension containing a compound of this invention may be adjusted to the desired pH, e.g., to a pH of 2 to 7, for example a pH of 2 to 5, using a suitable acid. Examples of suitable inorganic acids include hydrochloric acid, hydrobromic acid, nitric acid, sulfuric acid and/or phosphoric acid. Examples of suitable organic acids include ascorbic acid, citric acid, malic acid, tartaric acid, maleic acid, succinic acid, fumaric acid, acetic acid, formic acid and propionic acid. If desired, mixtures of the above acids may be used, particularly in the case of acids which have other properties in addition to their acidifying qualities, e.g. as flavorings, antioxidants or complexing agents, such as citric acid or ascorbic acid, for example.

Co-solvents and/or other excipients may be added to the propellant-free inhalable solutions according to the invention. Suitable co-solvents include, but are not limited to, those which contain hydroxyl groups or other polar groups such as alcohols (e.g., isopropyl alcohol), glycols (such as propylene glycol, polyethylene glycol, polypropylene glycol, glycol ether, glycerol), polyoxyethylene alcohols, and polyoxyethylene fatty acid esters. Suitable excipients include substances that have no pharmacological effect or, in connection with the desired therapy, no appreciable or at least no undesirable pharmacological effect. The excipients and additives include, but are not limited to, surfactants such as soya lecithin, oleic acid, sorbitan esters, such as polysorbates, polyvinylpyrrolidone, stabilizers, complexing agents, antioxidants (for example, ascorbic acid vitamin A, vitamin E, tocopherols and similar vitamins) and/or preservatives which guarantee or prolong the shelf life of the finished pharmaceutical formulation, flavorings, vitamins, pharmacologically acceptable salts such as sodium chloride as isotonic agents, and/or other additives known in the art.

Preservatives may be used to protect the propellant-free inhalable solutions according to the invention from contamination with pathogens. Suitable preservatives include, but are not limited to, cetyl pyridinium chloride, benzalkonium chloride or benzoic acid or benzoates such as sodium benzoate. The preservatives may be present in concentrations of up to 50 mg/100 mL, for example between 5 and 20 mg/100 mL.

The propellant-free inhalable solutions according to the invention can be administered, for example, using inhalers of the kind which are capable of nebulizing a small amount of a liquid formulation in the therapeutic dose within a few seconds to produce an aerosol suitable for therapeutic inhalation. For example, suitable inhalers are those in which a quantity of less than 100 μL, as a further example less than 50 μL, and as a further example between 10 and 30 μL of the propellant free solution can be nebulized in one spray action to form an aerosol with an average particle size of less than 20 μm, for example less than 5 μm, in such a way that the inhalable part of the aerosol corresponds to the therapeutically effective quantity. For example, in certain embodiments the average particle size in the range of about 1.0 to 4.4 microns.

A suitable apparatus of this kind for propellant-free delivery of a metered quantity of a liquid pharmaceutical composition for inhalation is described for example in U.S. Pat. Nos. 6,402,055; 6,497,373; and 5,964,416. The nebulizers described therein are known by the name Respimat®. Other suitable devices for nebulizing the propellant-free solutions include jet-stream inhalers and other stationary nebulizers.

Accordingly, in a further aspect, the invention relates to pharmaceutical formulations in the form of propellant-free inhalable solutions or suspensions as described above combined with a device suitable for administering these formulations. In certain embodiments, the invention relates to propellant-free inhalable solutions or suspensions characterized by the combination of a compound of this invention in conjunction with a device described for example in U.S. Pat. Nos. 6,402,055; 6,497,373; and 5,964,416.

The propellant-free inhalable solutions or suspensions according to the invention may take the form of concentrates or sterile inhalable solutions or suspensions ready for use, as well as the above-mentioned solutions and suspensions designed for use in Respimat®. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterized in that the device is an energy-operated free-standing or portable nebulizer which produces inhalable aerosols by means of ultrasound or compressed air by the Venturi principle or other methods.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In general, the amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press, 1990, which is specifically incorporated herein by reference.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Articles of Manufacture

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of this invention can be used to treat a p38 kinase-mediated disease or disorder. The label or package insert may also indicate that the composition can be used to treat other disorders.

In certain embodiments, the kits are suitable for the delivery of solid oral forms of a compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of this invention contained therein; and (b) a second container with a second pharmaceutical formulation contained therein, wherein the second pharmaceutical formulation comprises a second compound useful for treating a p38 kinase-mediated disease or disorder. Alternatively, or additionally, the kit may further comprise a third container comprising a pharmaceutically-acceptable buffer, such as bacteriostatic water for injection (BWFI), phosphate-buffered saline, Ringer's solution and dextrose solution. The kit may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising a compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second pharmaceutical formulation, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, this invention also includes a kit for treating a p38 kinase mediated disease or condition comprising: (a) a first pharmaceutical composition comprising a compound of this invention; and (b) instructions for use.

In one embodiment, the kit further comprises (c) a second pharmaceutical composition, wherein the second pharmaceutical composition comprises a second p38 inhibitor. In certain embodiments, the kit further comprising instructions for the simultaneous, sequential or separate administration of said first and second pharmaceutical compositions to a patient in need thereof. In certain embodiments, said first and second pharmaceutical compositions are contained in separate containers. In certain embodiments, said first and second pharmaceutical compositions are contained in the same container Biological Activity In general, the activity of the compounds of this invention may be assayed for p38 MAPK inhibition in vitro, in vivo, or in a cell line. In vitro assays include assays that determine inhibition of either the kinase activity or ATPase activity of activated p38 MAPK. Alternate in vitro assays quantitate the ability of the inhibitor to bind to p38 MAPK and may be measured either by radiolabelling the inhibitor prior to binding, isolating the inhibitor/p38 MAPK complex and determining the amount of radiolabel bound, or by running a competition experiment where new inhibitors are incubated with p38 MAPK bound to known radioligands. These and other useful in vitro and cell culture assays are well known to those of skill in the art.

Cell culture assays of the inhibitory effect of the compounds of this invention may be used to determine the amounts of TNF-α, IL-1, IL-6 or IL-8 produced in whole blood or cell fractions thereof in cells treated with inhibitor as compared to cells treated with negative controls. Levels of these cytokines may be determined through the use of commercially available ELISAs.

BIOLOGICAL EXAMPLES

The biological activities of the compounds of the invention were demonstrated by the following in vitro assays.

Example A p38 Biochemical Assay

P38 activity was assayed at room temperature in a 100 μL reaction containing 5 nM activated p38α enzyme and 1 μM ATF-2 (Activating Transcription Factor 2 fusion protein) as the substrate in 25 mM HEPES (pH 7.4), 100 μM Vanadate, 1 mM DTT, 10 mM $MgCl_2$ and 10 μM [γ-$^{33}$P]-ATP (~0.1 μCi $P^{33}$/reaction). The reaction was terminated after 30-40 minutes by adding 25% TCA, allowed to stand for 5 minutes and then transferred directly to a GF-B membrane filter plate. The filter was washed twice for 30 seconds with 0.5% phosphoric acid using a Tomtec Mach III Automated Harvestor. After washing, the vacuum was continued for 30 seconds to dry the filter. Approximately 30 μL of scintillant was added per well to the filter plate and then read in a Liquid Scintillation Counter (Packard TopCount HTS). All compounds exemplified herein had an $EC_{50}$ as determined by this assay of 10 μM or less.

Example B

Human Whole Blood TNF-α Assay

Compound test solutions were made by making 3.33 fold serial dilutions in DMSO, which dilutions were then diluted to 5× stocks by diluting with MEM, 2% heat inactivated fetal bovine serum ("FBS"), 20 mM HEPES, 2 mM L-glutamine, and 1% penicillin/streptomycin.

Whole blood was collected from human volunteers using sodium heparin Vacutainer™ tubes and processed within two hours of collection. Blood was diluted 3-fold with Whole Blood (WB) medium (RPMI 1640, 2% heat inactivated fetal bovine serum, 20 mM HEPES, 2 mM L-glutamine, and 1% penicillin/streptomycin). 100 μL of diluted blood was added to each well of a 96-well cell culture plate, followed by 30 μL of a compound test solution.

After a one-hour incubation at 37° C./5% $CO_2$, 20 μL of 7.5 ng/mL lipopolysaccharide (E. coli K-235, Sigma L2018) was added to each well. The cells were incubated again at 37° C./5% $CO_2$ for 16-20 hours. The test compound supernatants were collected and assayed for TNF-α content by ELISA methods. Briefly, test compound supernatants were added to wells of a 96-well plate that were coated with antibody to human TNF-α (R&D Systems, MAB210) and incubated at room temperature for at least one hour. After washing with wash buffer, wells were incubated at room temperature with 100 μL of 0.2 μg/mL biotinylated goat anti-human TNF-α (R&D Systems, BAF210) in "antibody diluent" (20 mM HEPES, pH 7.4, 150 nM NaCl, 2 mM $MgCl_2$, 1% BSA, 0.02% Tween-20) for another hour. After washing, the plate was incubated with 100 μL of 0.02 μg/mL streptavidin-alkaline phosphatase in antibody diluent for an additional hour. 200 μL of the colorimetric substrate p-nitrophenyl phosphate (pNPP, 1 mg/mL) in diethanolamine buffer with 0.5 mM $MgCl_2$ was added to each well. After incubation at room temperature for 30-40 minutes, the reaction was stopped by the addition of 2N NaOH. The absorbance at 405 nm was then read. All compounds exemplified herein had an $IC_{50}$ as determined by this assay of 10 μM or less.

Preparative Examples

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other p38 inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius.

Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H NMR spectra were recorded on a Varian instrument operating at 400 MHz. $^1$H NMR spectra were obtained as $CDCl_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

General Procedure for the Synthesis of Lactam Intermediates (4)

The general synthesis of lactam intermediates (4) suitable for use in the preparation of compounds of Formula I is shown in Scheme 2. An appropriated amino acid (3) (22.6 mmol) is added to a stirring solution of hexamethyldisilazide (46 mL, 9.8 mmol) in acetonitrile (95 mL) in a round bottom flask equipped with a reflux condenser under an atmosphere of dry nitrogen. The reaction is heated to reflux for 2 days, and then allowed to cool to ambient temperature. The crude reaction mixture is poured onto ice-cold methanol, and allowed to warm to ambient temperature. The reaction mixture is concentrated and diluted with chloroform. The suspension is filtered, and the filtrated is concentrated to yield the lactam intermediate (4).

Example 2

Preparation of (S)-3-aminopyrrolidin-2-one (4a)

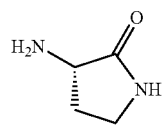

(S)-3-aminopyrrolidin-2-one was prepared from (s)-2,4-diaminobutanoic acid hydrochloride according to the general procedure of Example 1 to provide the desired product in 70.6% yield.

Example 3

Preparation of (S)-3-aminopiperidin-2-one (4b)

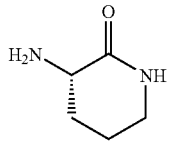

(S)-3-aminopiperidin-2-one was prepared from L-ornithine to provide the desired product in 82% yield.

Example 4

(S)-3-Aminoazepan-2-one (4c)

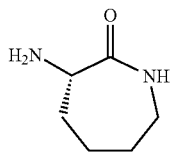

This compound is commercially available from Aldrich.

Example 5

General Procedure for the Synthesis of Protected Lactam Intermediates (5)

The general synthesis of protected lactam intermediates (5) is shown in Scheme 2. Lactam (4) (6.5 mmol; prepared according to the general method of Example 1) is added to a solution of BOC anhydride (1.5 g, 6.9 mmol) and triethylamine (0.96 mL, 6.9 mmol) in dichloromethane (30 mL) in a round-bottom flask and the reaction is allowed to stir at ambient temperature for 16 hours. The reaction mixture is concentrated and precipitated with ether. The slurry is filtered, and the solids are dissolved in dichloromethane, filtered, and concentrated to yield the BOC-protected lactam (5).

Example 6

Preparation of (S)-tert-butyl 2-oxopyrrolidin-3-ylcarbamate (5a)

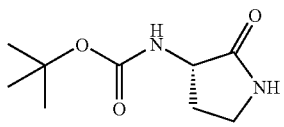

(S)-tert-butyl 2-oxopyrrolidin-3-ylcarbamate was prepared from compound (S)-3-aminopyrrolidin-2-one (Example 2) according to the general procedure of Example 5 to provide the desired compound in 74% yield.

Example 7

Preparation of (S)-tert-butyl 2-oxopiperidin-3-ylcarbamate (5b)

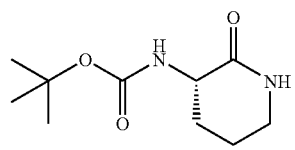

(S)-tert-butyl 2-oxopiperidin-3-ylcarbamate was prepared from compound (S)-3-aminopiperidin-2-one (Example 3) according to the general procedure of Example S to provide the desired compound in 67% yield.

Example 8

Preparation of (S)-tert-butyl 2-oxoazepan-3-ylcarbamate (5c)

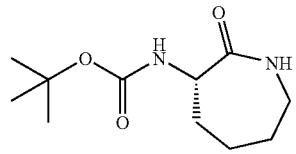

(S)-tert-butyl 2-oxoazepan-3-ylcarbamate was prepared from compound (S)-3-aminoazepan-2-one (Example 4) according to the general procedure of Example 5 to provide the desired compound in 61% yield.

Example 9

General Procedure for the Synthesis of Alkylated Protected Lactam Intermediates (2)

The general synthesis of alkylated protected lactam intermediates (2) is shown in Scheme 2. To a suspension of sodium hydride (60% in mineral oil, 66 mg, 1.7 mmol) in tetrahydrofuran (0.8 mL) at ambient temperature is added a solution of the protected lactam (5) prepared according to Example 5 (1.5 mmol), and either methyl iodide or (2-bromoethoxy)(tert-butyl)dimethylsilane (1.6 mmol) in tetrahydrofuran (3 mL) and N,N-dimethylformamide (3 mL) is added dropwise over 10 minutes. The reaction is allowed to stir at ambient temperature for 16 hours. The reaction mixture is concentrated and diluted with ethyl acetate, washed with water and brine, dried over Na₂SO₄, filtered, and concentrated. The crude product is purified by flash chromatography to yield the protected lactam.

Example 10

Preparation of (S)-tert-butyl 1-methyl-2-oxopyrrolidin-3-ylcarbamate (2a)

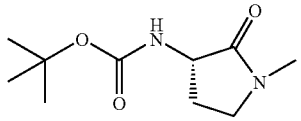

(S)-tert-butyl 1-methyl-2-oxopyrrolidin-3-ylcarbamate was prepared from compound (S)-tert-butyl 2-oxopyrrolidin-3-ylcarbamate (Example 6) and methyl iodide according to the general procedure of Example 9. The crude product was purified by column chromatography, eluting with 25% acetone/hexanes to provide compound (2a) in 45% yield.

Example 11

Preparation of (S-tert-butyl 1-(2-(tert-butyldimethylsilyloxy)ethyl)-2-oxopyrrolidin-3-ylcarbamate (2b)

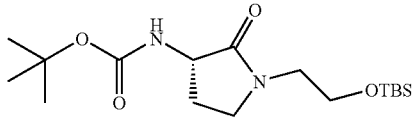

(S)-tert-butyl 1-(2-(tert-butyldimethylsilyloxy)ethyl)-2-oxopyrrolidin-3-ylcarbamate was prepared from compound (s)-tert-butyl 2-oxopyrrolidin-3-ylcarbamate (Example 6) and (2-bromoethoxy)(tert-butyl)dimethylsilane according to the general procedure of Example 9. The crude product was purified by column chromatography, eluting with 80% ethyl acetate/hexanes, to provide compound (2b) in 37% yield.

Example 12

Preparation of (S)-tert-butyl 1-methyl-2-oxopiperidin-3-ylcarbamate (2c)

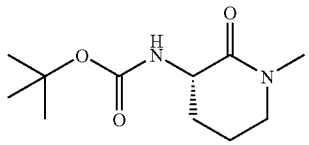

(S)-tert-butyl 1-methyl-2-oxopiperidin-3-ylcarbamate was prepared from (S)-tert-butyl 2-oxopiperidin-3-ylcarbamate (Example 7) and methyl iodide according to the general procedure of Example 9. The crude product was purified by column chromatography, eluting with 100% ethyl acetate, to provide compound (2c) in 31% yield.

Example 13

Preparation of (S)-tert-butyl 1-(2-(tert-butyldimethylsilyloxy)ethyl)-2-oxopiperidin-3-ylcarbamate (2d)

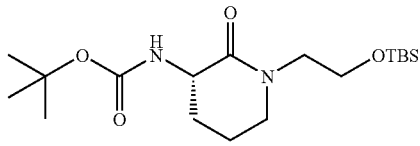

(S)-tert-butyl 1-(2-(tert-butyldimethylsilyloxy)ethyl)-2-oxopiperidin-3-ylcarbamate was prepared from (S)-tert-butyl 2-oxopiperidin-3-ylcarbamate (Example 7) and (2-bromoethoxy)(tert-butyl)dimethylsilane according to the general procedure of Example 9. The crude product was purified by column chromatography, eluting with 50% ethyl acetate/hexanes, to provide compound (2d) in 26% yield.

Example 14

Preparation of (S)-tert-butyl 1-methyl-2-oxoazepan-3-ylcarbamate (2e)

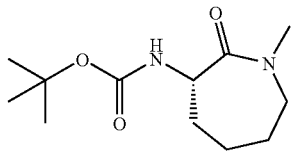

(S)-tert-butyl 1-methyl-2-oxoazepan-3-ylcarbamate was prepared from (S)-tert-butyl 2-oxoazepan-3-ylcarbamate (Example 8) and methyl iodide according to the general procedure of Example 9. The crude product was purified by column chromatography, eluting with 50% ethyl acetate/hexanes, to provide compound (2e) in 48% yield.

Example 15

Preparation of (S)-tert-butyl 1-(2-(tert-butyldimethylsilyloxy)ethyl)-2-oxoazepan-3-ylcarbamate (2f)

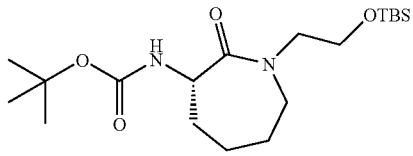

(S)-tert-butyl 1-(2-(tert-butyldimethylsilyloxy)ethyl)-2-oxoazepan-3-ylcarbamate was prepared from compound (S)-tert-butyl 2-oxoazepan-3-ylcarbamate (Example 8) and (2-bromoethoxy)(tert-butyl)dimethylsilane according to the general procedure of Example 9. The crude product was purified by column chromatography, eluting with 25% ethyl acetate/hexanes, to provide compound (2f) in 48% yield.

Example 16

Preparation of (S)-5-(2,4-difluorophenoxy)-1-isobutyl-N-(2-oxopyrrolidin-3-yl)-1H-indazole-6-carboxamide (Ia)

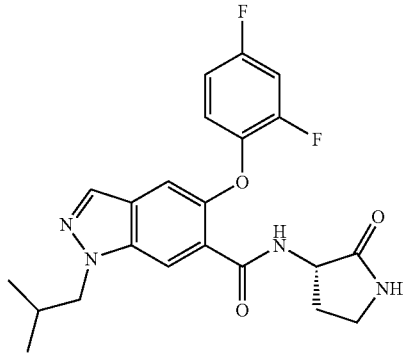

Step A: 1,2-Dibromo-4-methyl-5-nitrobenzene: 3,4-dibromotoluene (108.11 mL, 800 mmol) was added dropwise with mechanical stirring over 4 hours to nitric acid (90%, 280 mL, 6000 mmol) that was cooled to 0° C. under a nitrogen atmosphere. The internal temperature of the mixture was maintained below 10° C. during the addition and the reaction mixture was stirred for 1 hour at 0° C. after completion of addition. Water (840 mL) was added drop-wise to the mixture while maintaining the internal temperature below 10° C. The crude product was collected by filtration and washed with water (5×500 mL) to remove the excess nitric acid. The solids were dried under high vacuum and purified by recrystallization from ethanol (800 mL) to provide 180.9 g (77% yield) of the desired product as a solid. $^1$H NMR (400 MHz, CDCl$_3$) δ 8.24 (s, 1H), 7.64 (s, 1H), 2.55 (s, 3H).

Step B: 1-Bromo-2-(2,4-difluorophenoxy)-4-methyl-5-nitrobenzene: A mixture of 1,2-dibromo-4-methyl-5-nitrobenzene (84.3 g, 286 mmol), 2,4-difluorophenol (37.2 g, 286 mmol), and K$_2$CO$_3$ (43.5 g, 315 mmol) were heated to 100° C. for 45 hours. The reaction mixture was cooled to room temperature and then stored in a 5° C. refrigerator overnight. The reaction mixture was poured into 1200 mL of ice water. The resulting damp solid was collected, partially ground up, and stirred in 900 mL H$_2$O for 45 minutes. The solid was collected by filtration and rinsed with 700 mL of water portion-wise. The resulting solid was dried under high vacuum overnight to yield 93.5 g of the desired product as a brown solid (95% yield). $^1$H NMR (400 MHz, CDCl$_3$) δ 8.38 (s, 1H), 7.18 (m, 1H), 7.03 (m, 1H), 6.97 (m, 1H), 6.52 (s, 1H), 2.50 (s, 3H).

Step C: 5-Bromo-4-(2,4-difluorophenoxy)-2-methylphenylamine: 1-Bromo-2-(2,4-difluorophenoxy)-4-methyl-5-nitrobenzene (87.0 g, 253 mmol) was dissolved in THF (300 mL) and diluted with MeOH (900 mL). Zinc dust (82.7 g, 1.26 mol) was added and 1 L of saturated NH$_4$Cl was added slowly so that the reaction temperature never exceeded 42° C. The reaction mixture was mechanically stirred vigorously for 16 hours, and the filtered through Celite and the filter cake was washed with ethyl acetate. The filtrate was then concentrated with 1.2 L of saturated NH$_4$OAc. The THF/MeOH was removed and the solids were collected and washed with water. The solids were then stirred in 1 L water for 30 minutes, then collected via filtration and rinsed with water (1 L) in three portions. The resulting solid was dried under high vacuum for 48 hours to produce 64 g of the desired product (81% yield). MS (ESI+) m/z 314, 316 (M+1, Br pattern) detected; $^1$H NMR (400 MHz, CDCl$_3$) δ 6.92 (m, 1H), 6.91 (s, 1H), 6.75 (m, 2H), 6.70 (s, 1H), 3.57 (br. s, 2H), 2.08 (s, 3H).

Step D: 6-Bromo-5-(2,4-difluoro-phenoxy)-1H-indazole
(i) 5-bromo-4-(2,4-difluorophenoxy)-2-methylbenzenediazonium tetrafluoroborate: 5-Bromo-4-(2,4-difluorophenoxy)-2-methylphenylamine (30.0 g, 96 mmol) was dissolved in 2:1 AcOH/H$_2$O (960 mL). NH$_4$BF$_4$ (20.0 g, 191 mmol) was added and the reaction mixture was cooled to 3° C. (~30 minutes). Concentrated HCl (40 mL) was then added, during which the mixture warmed to 6° C. The mixture was cooled to 2° C. and then NaNO$_2$ (7.25 g, 105 mmol) was added. The reaction mixture was stirred in an ice bath for 5 minutes and then allowed to stir for 1 hour at room temperature. The mixture was concentrated under reduced pressure and the residue was azeotroped with toluene (3×400 mL). The crude material was used in the next reaction without further purification.
(ii) 6-Bromo-5-(2,4-difluorophenoxy)-1H-indazole: The crude 5-bromo-4-(2,4-difluorophenoxy)-2-methylbenzenediazonium tetrafluoroborate was suspended in ethyl acetate (650 mL) and treated with 10 equivalents of KOAc. The mixture was vigorously stirred at room temperature for 1.5 hours and then filtered and diluted to a 1 L total volume with ethyl acetate. The mixture was washed with saturated NaHCO$_3$/brine (800 mL, 1:1). The aqueous phase was extracted with ethyl acetate (400 mL). The organics were combined, dried (MgSO$_4$) and concentrated to provide the desired product as a brown solid (31 g, 99% yield). $^1$H NMR (400 MHz, CDCl$_3$) δ 10.55 (br. s, 1H), 7.98 (s, 1H), 7.84 (s, 1H), 7.20 (s, 1H), 6.99 (m, 1H), 6.94 (m, 1H), 6.84 (m, 1H).

Step E: 6-Bromo-5-(2,4-difluorophenoxy)-1-isobutyl-1H-indazole: 6-Bromo-5-(2,4-difluorophenoxy)-1H-indazole (60.0 g, 185 mmol) was dissolved in DMF and treated with K$_2$CO$_3$ (76.5 g, 554 mmol) and isobutyl bromide (126.4 g, 923 mmol). The reaction mixture was stirred and heated to 80° C. for 16 hours. An additional 15 g of K$_2$CO$_3$ were added and the mixture was vigorously stirred for an additional 24 hours, then cooled to room temperature and filtered. The filtrate was concentrated under reduced pressure and dissolved in ether (1 L). The ether layer was washed with 1:5 brine/water (2×600 mL). The aqueous phases were extracted with ether (300 mL) and the combined organic layers were dried (MgSO$_4$) and concentrated under reduced pressure. The crude product was chromatographed on a Biotage Flash 75 in two batches (about 35 g each) eluting with 5% ethyl acetate in hexanes. The combined purified products yielded 30.1 g of the desired product as a solid (43% yield). MS (ESI+) m/z 381, 383 (M+1, Br pattern) detected; $^1$H NMR (400 MHz, CDCl$_3$) δ 7.86 (s, 1H), 7.72 (s, 1H), 7.16 (s, 1H), 6.98 (m, 1H), 6.92 (m, 1H), 6.82 (m, 1H), 4.12 (d, 2H), 2.34 (m, 1H), 0.94 (d, 6H).

Step F: 5-(2,4-Difluorophenoxy)-1-isobutyl-1H-indazole-6-carbonitrile: 6-Bromo-5-(2,4-difluorophenoxy)-1-isobutyl-1H-indazole (31.2 g, 82 mmol) and Cu(I)CN (13.9 g, 156 mmol) were dissolved in DMA and degassed with nitrogen under vacuum. The reaction mixture was heated to 150° C. for 16 hours. The mixture was then cooled to room temperature and diluted with ethyl acetate before washing twice with 7M NH$_4$OH. The organic layer was washed with brine and degassed with nitrogen before being dried over MgSO$_4$ and concentrated under reduced pressure. The crude product was chromatographed eluting with 10% ethyl acetate in hexanes to afford 25.1 g of the desired product (95% yield).

Step G: 5-(2,4-Difluorophenoxy)-1-isobutyl-1H-indazole-6-carboxylic acid: 5-(2,4-Difluorophenoxy)-1-isobutyl-1H-indazole-6-carbonitrile (25.1 g, 77 mmol) was suspended in ethanol (620 mL) and KOH (2.5 M, 310 mL) and heated to reflux for 24 hours. The reaction mixture was cooled to room temperature and the ethanol was removed under reduced pressure. The resulting aqueous solution was diluted with water and washed with ether. The aqueous layer was acidified with concentrated HCl to pH 1 and extracted with ethyl acetate several times. The organic layers were combined and concentrated under reduced pressure to afford 25.5 g of the desired product (96% yield).

$^1$H NMR (400 MHz, CDCl$_3$) δ 8.37 (s, 1H), 7.91 (s, 1H), 7.20 (m, 1H), 7.07 (s, 1H), 7.04 (m, 1H), 6.95 (m, 1H), 4.24 (d, 2H), 2.36 (m, 1H), 0.94 (d, 6H).

Step H: 5-(2,4-difluorophenoxy)-1-isobutyl-1H-indazole-6-carboxylic acid 2,5-dioxopyrrolidin-1-yl ester: 5-(2,4-Difluorophenoxy)-1-isobutyl-1H-indazole-6-carboxylic acid (39.5 g, 113.9 mmol), N-hydroxysuccinimide (17.0 g, 148 mmol) and EDCI (26.0 g, 137 mmol) were dissolved in CH$_2$Cl$_2$ (200 mL). The solution was stirred for 3 hours and then was diluted with 100 mL CH$_2$Cl$_2$ and washed sequentially with a saturated NH$_4$Cl solution, twice with a saturated Na$_2$CO$_3$ solution, and once with brine. The organics were dried (MgSO$_4$), filtered, and concentrated under reduced pressure. The crude residue was precipitated from Et$_2$O to afford 41.0 g of 5-(2,4-difluorophenoxy)-1-isobutyl-1H-indazole-6-carboxylic acid 2,5-dioxopyrrolidin-1-yl ester (81% yield). $^1$H NMR (400 MHz, CDCl$_3$) δ 8.26 (s, 1H), 7.95 (s, 1H), 7.20 (s, 1H), 7.05-6.94 (m, 2H), 6.88-6.81 (m, 1H), 4.24 (d, J=7.83 Hz, 2H), 2.90 (s, 4H), 2.43-2.32 (m, 1H), 0.96 (d, J=7.04 Hz, 6H).

Step I: Synthesis of (S)-5-(2,4-difluorophenoxy)-1-isobutyl-N-(2-oxopyrrolidin-3-yl)-1H-indazole-6-carboxamide (Ia); To a solution of 2,5-dioxopyrrolidin-1-yl 5-(2,4-difluorophenoxy)-1-isobutyl-1H-indazole-6-carboxylate (700 mg, 1.58 mmol) in dichloromethane (5 mL) was added (S)-3-aminopyrrolidin-2-one (prepared according to Example 2; 205 mg, 2.05 mmol) and the reaction was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on a silica gel column, eluting with a gradient of 25-100% acetone/hexanes to yield (S)-5-(2,4-difluorophenoxy)-1-isobutyl-N-(2-oxopyrrolidin-3-yl)-1H-indazole-6-carboxamide (Ia) (520 mg, 77%). Mass spec: 429 (M+1). $^1$H NMR (CDCl$_3$) δ 8.37 (s, 1H), 8.26 (d, 1H), 7.87 (s, 1H), 7.15 (m, 1H), 7.03 (s, 1H), 7.00 (m, 1H), 6.91 (m, 1H), 6.03 (br, 1H), 4.59 (ddd, 1H), 4.22 (d, 2H), 3.46 (m, 2H), 2.87 (m, 1H), 2.36 (m, 1H), 2.10 (m, 1H), 0.92 (d, 6H).

Example 17

Preparation of (g)-5-(2,4-difluorophenoxy)-1-isobutyl-N-(2-oxopiperidin-3-yl)-1H-indazole-6-carboxamide (Ib)

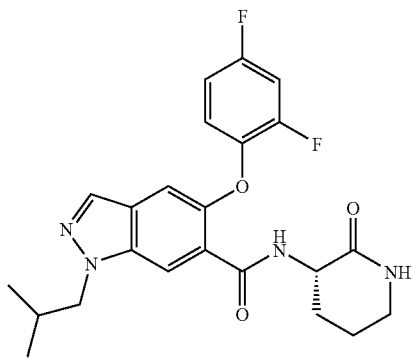

To a solution of 2,5-dioxopyrrolidin-1-yl-5-(2,4-difluorophenoxy)-1-isobutyl-1H-indazole-6-carboxylate (prepared according to Example 16; 1.01 g, 2.28 mmol) in dichloromethane (10 mL) was added (S)-3-aminopiperidin-2-one (prepared according to Example 3; 521 mg, 4.56 mmol) and the reaction was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on a silica gel column, eluting with a gradient of 50-100% acetone/hexanes to yield (S)-5-(2,4-difluorophenoxy)-1-isobutyl-N-(2-oxopiperidin-3-yl)-1H-indazole-6-carboxamide (Ib) (1.00 g, 99%). Mass spec: 443 (M+1). $^1$H NMR (CDCl$_3$) δ 8.58 (br, 1H), 8.34 (s, 1H), 7.87 (s, 1H), 7.15 (m, 1H), 7.04 (s, 1H), 7.00 (m, 1H), 6.89 (m, 1H), 5.80 (br, 1H), 4.51 (ddd, 1H), 4.22 (d, 2H), 3.38 (m, 2H), 2.70 (m, 1H), 2.36 (m, 2H), 1.99 (m, 2H), 1.70 (m, 1H), 0.93 (d, 6H).

Example 18

Preparation of (S)-5-(2,4-difluorophenoxy)-1-isobutyl-N-(2-oxoazepan-3-yl)-1H-indazole-6-carboxamide (Ic)

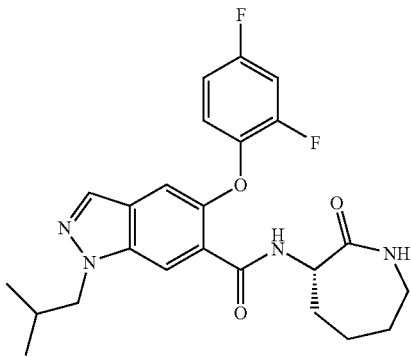

To a solution of 2,5-dioxopyrrolidin-1-yl-5-(2,4-difluorophenoxy)-1-isobutyl-1H-indazole-6-carboxylate (Example 16; 300 mg, 0.677 mmol) in dichloromethane (3 mL) was added (S)-3-aminoazepan-2-one (prepared according to Example 4; 173 mg, 1.35 mmol) and the reaction was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on a silica gel column, eluting with 80% ethyl acetate/hexanes to yield (S)-5-(2,4-difluorophenoxy)-1-isobutyl-N-(2-oxoazepan-3-yl)-1H-indazole-6-carboxamide (Ic) (290 mg, 94%). Mass spec: 457 (M+1). $^1$H NMR (CDCl$_3$) δ 9.11 (br, 1H), 8.33 (s, 1H), 7.86 (s, 1H), 7.16 (m, 1H), 7.04 (s, 1H), 7.00 (m, 1H), 6.89 (m, 1H), 6.14 (br, 1H), 4.78 (ddd, 1H), 4.22 (d, 2H), 3.34 (m, 1H), 3.24 (m, 1H), 2.35 (m, 1H), 2.26 (m, 1H), 2.07 (m, 1H), 1.89 (m, 2H), 1.57 (m, 1H), 1.42 (m, 1H), 0.93 (d, 6H).

Example 19

Metabolite of Compound Exemplified in WO 04/078116

Preparation of (S)-5-(2,4-difluorophenoxy)-1-isobutyl-N-(1-methyl-2-oxopyrrolidin-3-yl)-1H-indazole-6-carboxamide (Id)

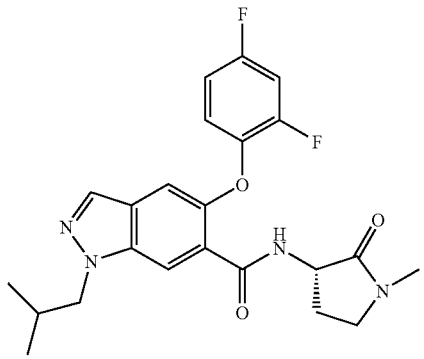

Step A: Synthesis of (S)-3-amino-1-methylpyrrolidin-2-one hydrochloride: (S)-tert-Butyl 1-methyl-2-oxopyrrolidin-3-ylcarbamate (prepared according to Example 10; 300 mg, 1.40 mmol) was dissolved in 4M hydrogen chloride in dioxane (3.5 mL, 14 mmol), and the reaction was allowed to stir at ambient temperature for 16 hours. The reaction mixture was concentrated to yield (S)-3-amino-1-methylpyrrolidin-2-one hydrochloride (211 mg, 100%) which was taken onto the next step without purification.

Step B: Synthesis of (S)-5-(2,4-difluorophenoxy)-1-isobutyl-N-(1-methyl-2-oxopyrrolidin-3-yl)-1H-indazole-6-carboxamide (Id): (S)-3-Amino-1-methylpyrrolidin-2-one hydrochloride (211 mg, 1.40 mmol) was dissolved in triethylamine (0.195 mL, 1.40 mmol) and dichloromethane (7 mL). To this, 2,5-dioxopyrrolidin-1-yl-5-(2,4-difluorophenoxy)-1-isobutyl-1H-indazole-6-carboxylate (prepared according to Example 16, Step A; 651 mg, 0.677 mmol) was added, and the reaction was allowed to stir at ambient temperature for 16 hours. The crude reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude product was purified by flash chromatography on a silica gel column, eluting with 25% acetone/hexanes to yield pure (S)-5-(2,4-difluorophenoxy)-1-isobutyl-N-(1-methyl-2-oxopyrrolidin-3-yl)-1H-indazole-6-carboxamide (Id) (360 mg, 58%). Mass spec: 443 (M+1). $^1$H NMR (CDCl$_3$) δ 8.36 (s, 1H), 8.29 (br, 1H), 7.18 (m, 1H), 7.01 (m, 2H), 6.92 (m, 1H), 4.56 (ddd, 1H), 4.22 (d, 2H), 3.42 (m, 2H), 2.93 (s, 3H), 2.82 (m, 1H), 2.37 (m, 1H), 1.99 (m, 1H), 0.92 (d, 6H).

Example 20

Preparation of (S)-5-(2,4-difluorophenoxy)-1-isobutyl-N-(1-methyl-2-oxopiperidin-3-yl)-1H-indazole-6-carboxamide (Ie)

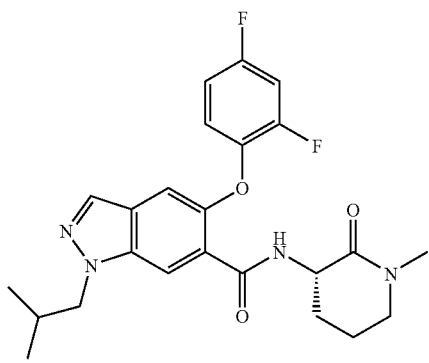

Step A: Synthesis of (S)-3-amino-1-methylpiperidin-2-one hydrochloride: (S)-tert-Butyl 1-methyl-2-oxopiperidin-3-ylcarbamate (prepared according to Example 12; 78 mg, 0.34 mmol) was dissolved in 4M hydrogen chloride in dioxane (1.7 mL, 6.8 mmol), and the reaction was allowed to stir at ambient temperature for 16 hours. The reaction mixture was concentrated to yield (S)-3-amino-1-methylpiperidin-2-one hydrochloride (56 mg, 100%), which was taken on to the next step without further purification.

Step B: Synthesis of (S)-5-(2,4-difluorophenoxy)-1-isobutyl-N-(1-methyl-2-oxopiperidin-3-yl)-1H-indazole-6-carboxamide (Ie): (S)-3-Amino-1-methylpiperidin-2-one hydrochloride (56 mg, 0.34 mmol) was dissolved in triethylamine (95 µL, 0.68 mmol) and N,N-dimethylformamide (1.5 mL). To this solution was added 2,5-dioxopyrrolidin-1-yl-5-(2,4-difluorophenoxy)-1-isobutyl-1H-indazole-6-carboxylate (prepared according to Example 16, Step A; 152 mg, 0.34 mmol), and the reaction mixture was allowed to stir at ambient temperature for 16 hours. The reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude product was purified by flash chromatography on a silica gel column, eluting with 70% ethyl acetate/hexanes to yield pure (S)-5-(2,4-difluorophenoxy)-1-isobutyl-N-(1-methyl-2-oxopiperidin-3-yl)-1H-indazole-6-carboxamide (Ie) (94 mg, 60%). Mass spec: 457 (M+1). $^1$H NMR (CDCl$_3$) δ 8.61 (br, 1H), 8.32 (s, 1H), 7.86 (s, 1H), 7.18 (m, 1H), 7.01 (m, 2H), 6.90 (m, 1H), 4.48 (ddd, 1H), 4.22 (d, 2H), 3.36 (m, 2H), 2.97 (s, 3H), 2.73 (m, 1H), 2.36 (m, 1H), 1.99 (m, 2H), 1.66 (m, 1H), 0.92 (d, 6H).

Example 21

Preparation of (S)-5-(2,4-difluorophenoxy)-1-isobutyl-N-(1-methyl-2-oxoazepan-3-yl)-1H-indazole-6-carboxamide (If)

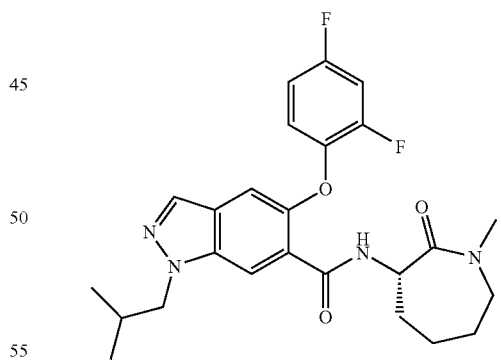

Step A: Synthesis of (S)-3-amino-1-methylazepan-2-one hydrochloride: To a solution of (S)-tert-butyl 1-methyl-2-oxoazepan-3-ylcarbamate (prepared according to Example 14; 0.152 g, 0.627 mmol) in dichloromethane (2 mL) was added 4M hydrogen chloride in dioxane (2 mL, 8 mmol), and the reaction mixture was allowed to stir overnight. The reaction mixture was concentrated to yield (S)-3-amino-1-methylazepan-2-one hydrochloride (0.112 g, 99.9% yield) which was taken on to the next step.

Step B: Synthesis of (S)-5-(2,4-difluorophenoxy)-1-isobutyl-N-(1-methyl-2-oxoazepan-3-yl)-1H-indazole-6-carboxamide: (S)-3-Amino-1-methylazepan-2-one hydrochloride (0.112 g, 0.627 mmol) was dissolved in triethylamine (0.238 mL, 1.71 mmol) and N,N-dimethylformamide (3 mL). To this was added 2,5-dioxopyrrolidin-1-yl-5-(2,4-difluorophenoxy)-1-isobutyl-1H-indazole-6-carboxylate (prepared according to Example 16, Step A; 253 mg, 0.570 mmol), and the reaction mixture was allowed to stir at ambient temperature for 16 hours. The reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude reaction mixture was purified by flash chromatography on a silica gel column, eluting with 60% ethyl acetate/hexanes to yield pure (S)-5-(2,4-difluorophenoxy)-1-isobutyl-N-(1-methyl-2-oxoazepan-3-yl)-1H-indazole-6-carboxamide (If) (208 mg, 78%). Mass spec: 471 (M+1). $^1$H NMR (CDCl$_3$) δ 9.15 (br, 1H), 8.32 (s, 1H), 7.85 (s, 1H), 7.21 (m, 1H), 6.99 (m, 2H), 6.92 (m, 1H), 4.91 (ddd, 1H), 4.21 (d, 2H), 3.67 (dd, 1H), 3.22 (dd, 1H), 3.04 (s, 3H), 2.35 (m, 1H), 2.21 (m, 1H), 2.05-1.81 (m, 3H), 1.54 (m, 1H), 1.45 (m, 1H), 0.92 (d, 6H).

Example 22

Preparation of (S)-5-(2,4-difluorophenoxy)-N-(1-(2-hydroxyethyl)-2-oxopyrrolidin-3-yl)-1-isobutyl-1H-indazole-6-carboxamide (Ig)

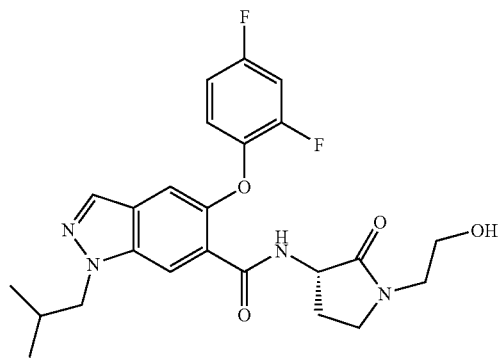

Step A: Synthesis of (±)-3-amino-1-(2-hydroxyethyl)pyrrolidin-2-one hydrochloride: (S)-tert-Butyl 1-(2-(tert-butyldimethylsilyloxy)ethyl)-2-oxopyrrolidin-3-ylcarbamate prepared according to Example 11; 200 mg, 0.558 mmol) was dissolved in 4M hydrogen chloride in dioxane (2.8 mL, 11.2 mmol), and the reaction mixture was allowed to stir at ambient temperature overnight. The reaction mixture was concentrated to yield (S)-3-amino-1-(2-hydroxyethyl)pyrrolidin-2-one hydrochloride (101 mg, 100%) which was taken on to the next step without further purification.

Step B: Synthesis of (S)-5-(2,4-difluorophenoxy)-N-(1-(2-hydroxyethyl)-2-oxopyrrolidin-3-yl)-1-isobutyl-1H-indazole-6-carboxamide: (S)-3-Amino-1-(2-hydroxyethyl)pyrrolidin-2-one hydrochloride (101 mg, 0.558 mmol) was dissolved in triethylamine (0.141 mL, 1.01 mmol) and N,N-dimethylformamide (2.5 mL). To this solution was added 2,5-dioxopyrrolidin-1-yl-5-(2,4-difluorophenoxy)-1-isobutyl-1H-indazole-6-carboxylate (prepared according to Example 16, Step A; 225 mg, 0.507 mmol), and the reaction mixture was allowed to stir at ambient temperature for 16 hours. The reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude product was purified by flash chromatography on silica gel, loaded and eluted with 100% acetone to yield pure (S)-5-(2,4-difluorophenoxy)-N-(1-(2-hydroxyethyl)-2-oxopyrrolidin-3-yl)-1-isobutyl-1H-indazole-6-carboxamide (Ig) (177 mg, 74%). Mass spec: 473 (M+1). $^1$H NMR (CDCl$_3$) δ 8.37 (br, 1H), 8.34 (s, 1H), 7.87 (s, 1H), 7.16 (m, 1H), 7.01 (m, 2H), 6.92 (m, 1H), 4.53 (m, 1H), 3.83 (m, 3H), 3.56 (m, 3H), 3.44 (m, 1H), 3.15 (t, 1H), 2.74 (m, 1H), 2.36 (m, 1H), 2.08 (m, 1H), 0.92 (d, 6H).

Example 23

Preparation of (S)-5-(2,4-difluorophenoxy)-N-(1-(2-hydroxyethyl)-2-oxopiperidin-3-yl)-1-isobutyl-1H-indazole-6-carboxamide (Ih)

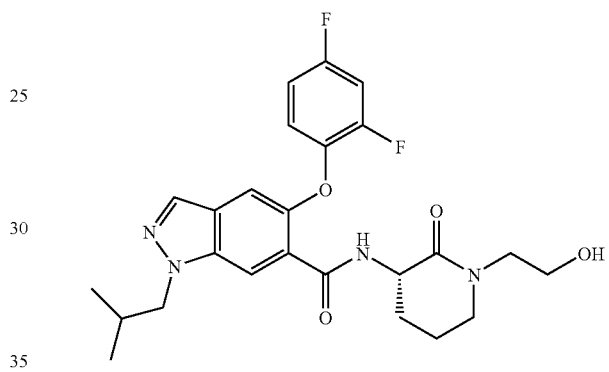

Step A: Synthesis of (S)-3-amino-1-(2-hydroxyethyl)piperidin-2-one hydrochloride: (S)-tert-Butyl 1-(2-(tert-butyldimethylsilyloxy)ethyl)-2-oxopiperidin-3-ylcarbamate (Example 13; 100 mg, 0.268 mmol) was dissolved in 4M hydrogen chloride in dioxane (2 mL, 8.0 mmol) and the reaction mixture was allowed to stir at ambient temperature for 72 hours. The reaction mixture was concentrated to yield (S)-3-amino-1-(2-hydroxyethyl)piperidin-2-one hydrochloride (52 mg, 100%) which was taken on to the next step without further purification.

Step B: Synthesis of (S)-5-(2,4-difluorophenoxy)-N-(1-(2-hydroxyethyl)-2-oxopiperidin-3-yl)-1-isobutyl-1H-indazole-6-carboxamide (Ih): (S)-3-Amino-1-(2-hydroxyethyl)piperidin-2-one hydrochloride (52 mg, 0.27 mmol) was dissolved in triethylamine (0.075 mL, 0.54 mmol) and N,N-dimethylformamide (1 mL). To this was added 2,5-dioxopyrrolidin-1-yl-5-(2,4-difluorophenoxy)-1-isobutyl-1H-indazole-6-carboxylate (prepared according to Example 16, Step A; 119 mg, 0.268 mmol), and the reaction mixture was allowed to stir at ambient temperature for 48 hours. The reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude product was purified by flash chromatography on a silica gel column, eluting with 50% acetone/hexanes to yield pure (S)-5-(2,4-difluorophenoxy)-N-(1-(2-hydroxyethyl)-2-oxopiperidin-3-yl)-1-isobutyl-1H-indazole-6-carboxamide (1 h) (104 mg, 80%). Mass spec: 487 (M+1). $^1$H NMR (CDCl$_3$) δ 8.57 (brd, 1H), 8.32 (s, 1H), 7.87 (s, 1H), 7.14 (m, 1H), 7.03 (s, 1H), 7.00 (m, 1H), 6.89 (m, 1H), 4.47 (ddd, 1H), 4.22 (d, 2H), 3.82 (m, 2H), 3.68 (m, 1H), 3.47 (m, 3H), 2.90 (m, 1H), 2.62 (m, 1H), 2.36 (m, 1H), 2.00 (m, 2H), 1.74 (m, 1H), 0.93 (d, 6H).

Example 24

Preparation of (S)-5-(2,4-difluorophenoxy)-N-(1-(2-hydroxyethyl)-2-oxoazepan-3-yl)-1-isobutyl-1H-indazole-6-carboxamide (Ii)

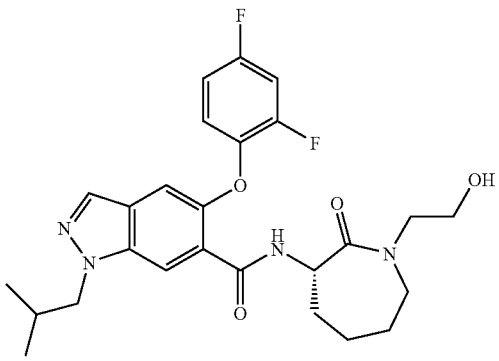

Step A: Synthesis of (S)-3-amino-1-(2-hydroxyethyl) azepan-2-one hydrochloride: To a solution of (S)-tert-butyl 1-(2-(tert-butyldimethylsilyloxy)ethyl)-2-oxoazepan-3-yl-carbamate (prepared according to Example 15; 243 mg, 0.629 mmol) in dichloromethane (2 mL) was added 4M hydrogen chloride in dioxane (2 mL, 8 mmol), and the reaction mixture was allowed to stir at ambient temperature for 16 hours. The reaction mixture was concentrated to yield (S)-3-amino-1-(2-hydroxyethyl)azepan-2-one hydrochloride (131 mg, 100%), which was taken on to the next reaction without further purification.

Step B: Synthesis of (S)-5-(2,4-difluorophenoxy)-N-(1-(2-hydroxyethyl-2-oxoazepan-3-yl)-1-isobutyl-1H-indazole-6-carboxamide (Ii): To a suspension of (S)-3-amino-1-(2-hydroxyethyl)azepan-2-one hydrochloride (131 mg, 0.629 mmol) in triethylamine (0.239 mL, 1.71 mmol) and N,N-dimethylformamide (3 mL) was added 2,5-dioxopyrrolidin-1-yl 5-(2,4-difluorophenoxy)-1-isobutyl-1H-indazole-6-carboxylate (Example 16, Step A; 253 mg, 0.571 mmol). The reaction mixture was allowed to stir at ambient temperature for 16 hours. 1M hydrochloric acid (2 mL) was added, and the reaction mixture was allowed to stir another 24 hours. The reaction mixture was diluted with ethyl acetate and washed with 1M hydrochloric acid, 1M sodium hydroxide, saturated sodium bicarbonate, and brine. The organic layer was dried over anhydrous sodium sulfate, filtered, and concentrated. The crude product was purified by flash chromatography on a silica gel column, eluting with 100% ethyl acetate to yield pure (S)-5-(2,4-difluorophenoxy)-N-(1-(2-hydroxyethyl)-2-oxoazepan-3-yl)-1-isobutyl-1H-indazole-6-carboxamide (Ii) (160 mg, 56%). Mass spec: 501 (M+1). $^1$H NMR (CDCl$_3$) δ 9.07 (brd, 1H), 8.31 (s, 1H), 7.86 (s, 1H), 7.15 (m, 1H), 7.00 (m, 2H), 6.89 (m, 1H), 4.93 (ddd, 1H), 4.22 (d, 2H), 3.79-3.65 (m, 4H), 3.55 (m, 1H), 3.34 (m, 1H), 2.64 (m, 1H), 2.35 (m, 1H), 2.21 (m, 1H) 2.0-1.85 (m, 3H), 1.55 (m, 2H), 0.92 (d, 6H).

Example 25

Preparation of (S)-5-(2,4-difluorophenoxy)-1-(2-hydroxy-2-methylpropyl)-N-(2-oxopyrrolidin-3-yl)-1H-indazole-6-carboxamide (Ij)

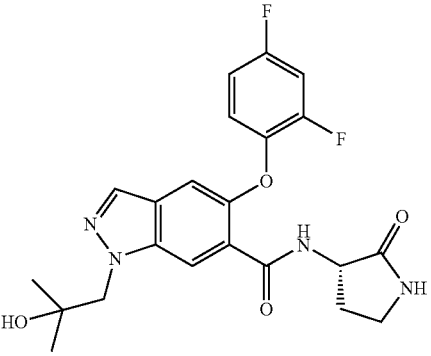

Step A: Synthesis of 6-bromo-5-(2,4-difluorophenoxy)-1H-indazole: Prepared from 6-Bromo-5-(2,4-difluorophenoxy)-1-isobutyl-1H-indazole according to Example 16, Steps A-D.

Step B: Synthesis of 1-(6-bromo-5-(2,4-difluorophenoxy)-1H-indazol-1-yl)-2-methylpropan-2-ol: To a solution of 6-bromo-5-(2,4-difluorophenoxy)-1H-indazole (1.35 g, 4.15 mmol) and 2,2-dimethyloxirane (0.755 mL, 8.30 mmol) in DMA (20 mL) in a sealed tube was added potassium carbonate (1.72 g, 12.5 mmol), and the reaction was heated to 80° C. for 16 hours. The reaction mixture was allowed to cool to ambient temperature, diluted with ethyl acetate, and washed twice with water and once with brine. It was dried over Na$_2$SO$_4$, filtered, and concentrated. The residue was purified by flash chromatography on silica gel loaded and eluted with 35% ethyl acetate/hexanes to yield pure 1-(6-bromo-5-(2,4-difluorophenoxy)-1H-indazol-1-yl)-2-methylpropan-2-ol (0.60 g, 36.4% yield).

Step C: Synthesis of 5-(2,4-difluorophenoxy)-1-(2-hydroxy-2-methylpropyl)-1H-indazole-6-carboxylic acid: To a solution of 1-(6-bromo-5-(2,4-difluorophenoxy)-1H-indazol-1-yl)-2-methylpropan-2-ol (0.691 g, 1.74 mmol) in 9:1 methanol/water v/v (11.6 mL) was added palladium (II) acetate (0.0195 g, 0.0870 mmol), 1-((3-(diphenylphosphino)propyl)(phenyl)phosphino)benzene (0.0359 g, 0.0870 mmol), and potassium carbonate (0.721 g, 5.22 mmol). The flask was evacuated and backfilled three times with carbon monoxide, and heated to 50° C. under a carbon monoxide balloon for S hours. The reaction mixture was acidified with 5N HCl and extracted twice with dichloromethane. The organic layer was concentrated, taken up in 5M NaOH, was washed twice with ethyl acetate, and then acidified to pH 1 with HCl. The organic layer was then extracted twice with ethyl acetate, dried over anhydrous sodium sulfate, filtered, and concentrated to yield 5-(2,4-difluorophenoxy)-1-(2-hydroxy-2-methylpropyl)-1H-indazole-6-carboxylic acid (0.280 g, 44.4% yield).

Step D: Synthesis of (S)-5-(2,4-difluorophenoxy)-1-(2-hydroxy-2-methylpropyl)-N-(2-oxopyrrolidin-3-yl)-1H-indazole-6-carboxamide (Ij): 5-(2,4-Difluorophenoxy)-1-(2- hydroxy-2-methylpropyl)-1H-indazole-6-carboxylic acid (200 mg, 0.552 mmol) was dissolved in N,N-dimethylformamide (2 mL). To his was added (S)-3-aminopyrrolidin-2-one (4a) (111 mg, 1.10 mmol), 4-(dimethylamino)pyridine (6.7 mg, 0.055 mmol), and 1-(3-dimethylaminopropyl)-3-ethylcarbodiimide hydrochloride (116 mg, 0.607 mmol) successively, and the reaction mixture was allowed to stir at ambient temperature for 16 hours. The reaction mixture was partitioned between water and ethyl acetate, and the aqueous layer was extracted twice with ethyl acetate. The combined organic layers were dried over anhydrous sodium sulfate, filtered, and concentrated. The crude product was purified by flash chromatography on a silica gel column, eluting with 100% acetone to yield pure (S)-5-(2,4-difluorophenoxy)-1-(2-hydroxy-2-methylpropyl)-N-(2-oxopyrrolidin-3-yl)-1H-indazole-6-carboxamide (Ij) (83 mg, 34%). Mass spec: 445 (M+1). $^1$H NMR (CDCl$_3$) δ 8.39 (s, 1H), 8.26 (brd, 1H), 7.93 (s, 1H), 7.18 (m, 1H), 7.04 (s, 1H), 7.02 (m, 1H), 6.92 (m, 1H), 6.04 (br, 1H), 4.59 (ddd, 1H), 4.37 (s, 2H), 3.64 (brs, 1H), 3.45 (m, 2H), 2.87 (m, 1H), 2.09 (m, 1H), 1.21 (s, 3H), 1.12 (s, 3H).

Example 26

Preparation of 2,5-dioxopyrrolidin-1-yl 5-(2,4-difluorophenoxy)-1-(2-fluoro-2-methylpropyl)-1H-indazole-6-carboxylate (1b)

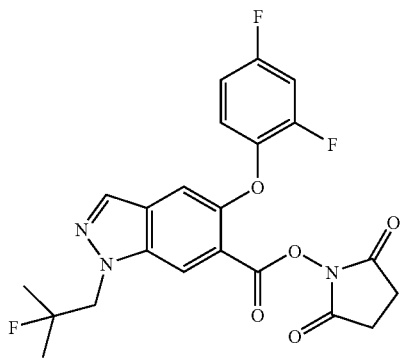

Step A: Synthesis of 6-bromo-5-(2,4-difluorophenoxy)-1-(2-fluoro-2-methylpropyl)-1H-indazole (6a): To a solution of (S)-5-(2,4-difluorophenoxy)-1-(2-hydroxy-2-methylpropyl)-N-(2-oxopyrrolidin-3-yl)-1H-indazole-6-carboxamide (prepared according to Example 26; 975 mg, 2.45 mmol) in dichloromethane (5 mL) at −78° C. was added diethylaminosulfur trifluoride (0.322 mL, 2.45 mmol) dropwise, and the reaction was allowed to stir for 30 minutes. The reaction was allowed to warm to ambient temperature and stirred for an additional hour. Following this, the reaction mixture was poured onto ice-cold diluted potassium hydroxide in water. The reaction mixture was allowed to warm to ambient temperature, and then extracted twice with ether. The combined organic layers were washed with brine, dried over anhydrous sodium sulfate, filtered, and concentrated. The crude product was purified by flash chromatography on silica gel and eluted with 10-20% EtOAc/hexanes to yield pure 6-bromo-5-(2,4-difluorophenoxy)-1-(2-fluoro-2-methylpropyl)-1H-indazole (6a) (744 mg, 75.9% yield).

Step B: Synthesis of 5-(2,4-difluorophenoxy)-1-(2-fluoro-2-methylpropyl)-1H-indazole-6-carboxylic acid (7a): 6-Bromo-5-(2,4-difluorophenoxy)-1-(2-fluoro-2-methylpropyl)-1H-indazole (1.64 g, 4.11 mmol) was dissolved in 9:1 methanol/water degassed with carbon monoxide (27 mL). To this was added 1-((3-(diphenylphosphino)propyl)(phenyl)phosphino)benzene (85 mg, 0.21 mmol), palladium (II) acetate (46 mg, 0.21 mmol), and potassium carbonate (1.70 g, 12.3 mmol). The reaction mixture was heated to 60° C. for 20 hours. The reaction mixture was then acidified to pH 1 by the addition of 5M hydrochloric acid, and the crude reaction mixture was partitioned between ether and water. The aqueous layer was extracted with ether, and the combined organic layers were washed with brine. The combined organic layers were dried over anhydrous sodium sulfate, filtered, and concentrated. The crude product was purified on a silica gel column, eluting with a gradient of 0.2-10% methanol/dichloromethane to yield 5-(2,4-difluorophenoxy)-1-(2-fluoro-2-methylpropyl)-1H-indazole-6-carboxylic acid (7a) (724 mg, 48%).

Step C: Synthesis of 2,5-dioxopyrrolidin-1-yl 5-(2,4-difluorophenoxy)-1-(2-fluoro-2-methylpropyl)-1H-indazole-6-carboxylate (Ib): To a solution of 5-(2,4-difluorophenoxy)-1-(2-fluoro-2-methylpropyl)-1H-indazole-6-carboxylic acid (0.724 g, 1.99 mmol) and 1-hydroxypyrrolidine-2,5-dione (0.297 g, 2.58 mmol) in dichloromethane (20 mL) was added N1-((ethylimino)methylene)-N3,N3-dimethylpropane-1,3-diamine hydrochloride (0.457 g, 2.38 mmol), and the reaction mixture was allowed to stir for 5 hours at ambient temperature. The reaction mixture was diluted with additional dichloromethane and washed with saturated ammonium chloride, saturated sodium carbonate, and brine. The reaction mixture was dried over anhydrous sodium sulfate, filtered, and concentrated. Ether was added, and hexanes were added to crystallize the product. The product was filtered to yield 2,5-dioxopyrrolidin-1-yl-5-(2,4-difluorophenoxy)-1-(2-fluoro-2-methylpropyl)-1H-indazole-6-carboxylate (Ib) (600 mg, 65.4% yield). Mass spec: 462 (M+1). $^1$H NMR (CDCl$_3$) δ 8.37 (s, 1H), 7.96 (s, 1H), 7.18 (s, 1H), 7.00 (m, 2H), 6.85 (m, 1H), 4.58 (d, 2H), 2.90 (br, 4H), 1.40 (d, 6H).

Example 27

Preparation of (S)-5-(2,4-difluorophenoxy)-1-(2-fluoro-2-methylpropyl)-N-(2-oxopyrrolidin-3-yl)-1H-indazole-6-carboxamide (Ik)

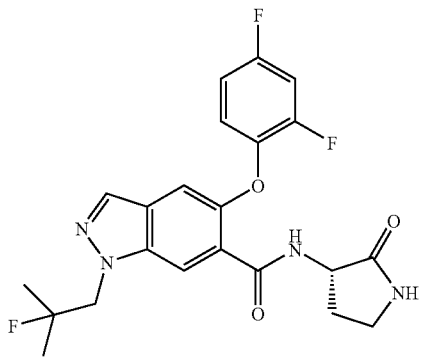

To a solution of 2,5-dioxopyrrolidin-1-yl-5-(2,4-difluorophenoxy)-1-(2-fluoro-2-methylpropyl)-1H-indazole-6-carboxylate (prepared according to Example 26; 100 mg, 0.217 mmol) in dichloromethane (1 mL) was added (S)-3-aminopyrrolidin-2-one (4a) 521 mg, 4.56 mmol), and the reaction mixture was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on a silica gel column, eluting with 50% acetone/hexanes to yield (S)-5-(2,4-difluorophenoxy)-1-(2-fluoro-2-methylpropyl)-N-(2-oxopyrrolidin-3-yl)-1H-indazole-6-carboxamide (Ik) (1.00 g, 99%). Mass spec: 447 (M+1). $^1$H NMR (CDCl$_3$) δ 8.42 (s, 1H), 8.21 (br, 1H), 7.15 (m, 1H), 7.03 (s, 1H), 7.01 (m, 1H), 6.91 (m, 1H), 6.59 (br, 1H), 4.58 (m, 1H), 4.55 (d, 2H), 3.43 (m, 2H), 2.84 (m, 1H), 2.06 (m, 1H), 1.40 (d, 3H), 1.39 (d, 3H).

Example 28

Preparation of (S)-5-(2,4-difluorophenoxy)-1-(2-fluoro-2-methylpropyl)-N-(2-oxopiperidin-3-yl)-1H-indazole-6-carboxamide (Il)

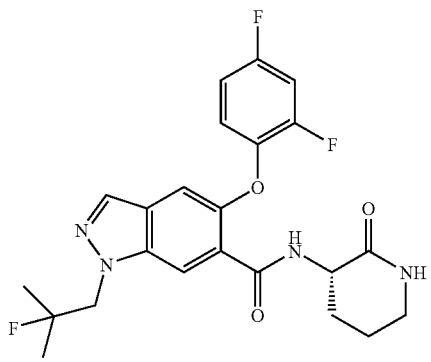

To a solution of 2,5-dioxopyrrolidin-1-yl-5-(2,4-difluorophenoxy)-1-(2-fluoro-2-methylpropyl)-1H-indazole-6-carboxylate (100 mg, 0.217 mmol; prepared according to Example 26) in dichloromethane (1 mL) was added (S)-3-aminopiperidin-2-one (prepared according to Example 3; 521 mg, 4.56 mmol), and the reaction mixture was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on silica gel, eluting with 50% acetone/hexanes to yield (S)-5-(2,4-difluorophenoxy)-1-(2-fluoro-2-methylpropyl)-N-(2-oxopiperidin-3-yl)-1H-indazole-6-carboxamide (Ik) (1.00 g, 99%). Mass spec: 461 (M+1). $^1$H NMR (CDCl$_3$) δ 8.53 (s, 1H), 8.40 (s, 1H), 7.90 (s, 1H), 7.15 (m, 1H), 7.03 (s, 1H), 6.99 (m, 1H), 6.90 (m, 1H), 6.09 (br, 1H), 4.56 (d, 1H), 4.53 (m, 1H), 3.36 (m, 2H), 2.70 (m, 1H), 1.97 (m, 1H), 1.66 (m, 1H), 1.39 (d, 3H), 1.38 (d, 3H).

Example 29

Preparation of (S)-5-(2,4-difluorophenoxy)-1-(2-fluoro-2-methylpropyl)-N-(2-oxoazepan-3-yl)-1H-indazole-6-carboxamide (Im)

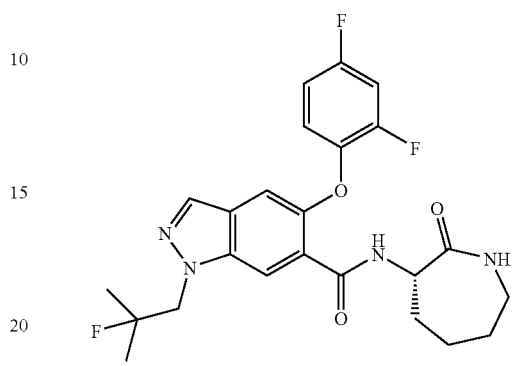

To a solution of 2,5-dioxopyrrolidin-1-yl 5-(2,4-difluorophenoxy)-1-(2-fluoro-2-methylpropyl)-1H-indazole-6-carboxylate (prepared according to Example 26; 100 mg, 0.217 mmol) in dichloromethane (1 mL) was added (S)-3-aminoazepan-2-one (prepared according to Example 4; 521 mg, 4.56 mmol) and the reaction mixture was allowed to stir overnight at ambient temperature. The reaction mixture was diluted with ethyl acetate and washed with 1M hydrochloric acid, 1M sodium hydroxide, saturated sodium bicarbonate, and saturated sodium chloride. The organic layer was dried over anhydrous sodium sulfate, filtered, and concentrated. The residue was purified by column chromatography on a silica gel column, eluting with 50% acetone/hexanes to yield (S)-5-*(2,4-difluorophenoxy)-1-(2-fluoro-2-methylpropyl)-N-(2-oxoazepan-3-yl)-1H-indazole-6-carboxamide (Ik) (1.00 g, 99%). Mass spec: 475 (M+1). $^1$H NMR (CDCl$_3$) δ 9.04 (brd, 1H), 8.38 (s, 1H), 7.90 (s, 1H), 7.16 (m, 1H), 7.03 (s, 1H), 7.00 (m, 1H), 6.89 (m, 1H), 6.23 (br, 1H), 4.77 (ddd, 1H), 4.56 (d, 2H), 3.33 (m, 1H), 3.22 (m, 1H), 2.25 (m, 1H), 2.05 (m, 1H), 1.89 (m, 2H), 1.56 (m, 1H), 1.42 (m, 1H), 1.40 (d, 3H), 1.39 (d, 3H).

Example 30

5-(2,4-difluorophenoxy)-1-isobutyl-N-(2-oxo-1,2-dihydropyridin-3-yl)-1H-indazole-6-carboxamide (In)

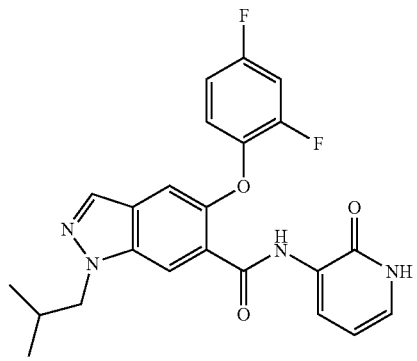

To a solution of 2,5-dioxopyrrolidin-1-yl-5-(2,4-difluorophenoxy)-1-isobutyl-1H-indazole-6-carboxylate (Example 16; 100 mg, 0.226 mmol) in dichloromethane (1.1 mL) was added 3-aminopyridin-2(1H)-one (26.1 mg, 0.237 mmol) and N-ethyl-N-isopropylpropan-2-amine (0.039 mL, 0.226 mmol). After 48 h, the reaction was treated with tris-amine resin (silica supported amine 3, 100 mg, loading=1.76 mmol/g). After 45 minutes, the reaction was filtered though a silica gel plug, washing well with ethyl acetate. The filtrate was washed with 1 N hydrochloric acid, saturated sodium bicarbonate, and saturated sodium chloride. The organics were dried with sodium sulfate, filtered and concentrated. The residue was purified by silica gel column chromatography, eluting with a gradient of 50% to 100% ethyl acetate/hexanes to yield 5-(2,4-difluorophenoxy)-1-isobutyl-N-(2-oxo-1,2-dihydropyridin-3-yl)-1H-indazole-6-carboxamide (32 mg, 32%). Mass spec: 439 (M+1). $^1$H NMR (CDCl$_3$) δ 10.8 (s, 1H), 8.68 (dd, 1H), 8.42 (s, 1H), 7.89 (s, 1H), 7.28-6.88 (m, 6H), 6.36 (dd, 1H), 4.25 (d, 2H), 2.38 (m, 1H), 0.95 (d, 6H).

Example 31

Alternative Synthesis of (S-5-(2,4-difluorophenoxy)-1-(2-fluoro-2-methylpropyl)-N-(2-oxopyrrolidin-3-yl)-1H-indazole-6-carboxamide (Ik)

Step A: Preparation of 1-(6-Bromo-5-(2,4-difluorophenoxy)-1H-indazol-1-yl)-2-methylpropan-2-ol: A 5 L pressure vessel fitted with a pressure relief valve, bursting disc, pressure gauge, and oil-filled thermometer well, and containing a 3"×½" octagonal stir bar was charged with a solution of 6-bromo-5-(2,4-difluorophenoxy)-1H-indazole (prepared according to Example 25, Steps A-D; 150 g, 0.46 mol) and isobutylene oxide (82 mL, 0.92 mol) in N,N-dimethylacetamide (1000 mL). The solution was magnetically stirred, and granular potassium carbonate (191 g, 1.38 mol) was added. The vessel was sealed and stirring was continued. The apparatus was placed behind a blast shield. The vessel was heated with a heating mantle connected to a J-Kem Model 150 temperature controller. The temperature setting was initially set to 55° C., and the temperature was increased to 80° C. over 6 hr. The temperature was maintained at 80° C. for a further 16 hr. The reaction mixture was then cooled to 28° C. and the vessel was opened. The thermometer well was removed and the reaction mixture was decanted from the inorganic salts and filtered through a coarse fritted sintered glass funnel. The salts that remained in the vessel were stirred with DMA (3×200 mL) and the solution decanted as before. The filtrates were combined and the solvent evaporated under reduced pressure to afford a dark brown oil. Meanwhile, the solid remaining in the vessel was partitioned between water (2000 mL) and diethyl ether (1000 mL), and the resulting mixture stirred for 16 hr. The water/ether mixture was transferred to a separatory funnel, and the organic layer was added to the brown oil. Additional ether (2000 mL) was added to completely dissolve the oil. The resulting solution was transferred to a separatory funnel and washed with a mixture of water (500 mL) and brine (500 mL). The organic layer was dried over magnesium sulfate and the solvent was removed under reduced pressure. The residual dark brown oil (an approximate 1:1 mixture of N-1 [less polar] and N-2 [more polar] regioisomers) was purified by chromatography on silica gel, using 70/30 EtOAc/hexanes as eluent. Fractions containing product were pooled and the solvent removed under reduced pressure to afford the title compound as a red-orange solid (93.8 g, 51%).

Step B: Preparation of 6-Bromo-5-(2,4-difluorophenoxy)-1-(2-fluoro-2-methylpropyl)-1H-indazole: A solution of 1-(6-Bromo-5-(2,4-difluorophenoxy)-1H-indazol-1-yl)-2-methylpropan-2-ol (19.8 g, 49.8 mmol) in DCM (150 mL) was cooled with a dry-ice acetone bath to −73° C. (Diaminoethyl)sulfur trifluoride (6.9 mL, 52.3 mmol) was added dropwise over 2 min; the temperature rose to −62° C. The resulting solution was stirred in the bath for a further 1 hr, then at ambient temperature for 1 hour. The reaction mixture was poured into a separatory funnel containing cold 10% KOH (250 mL), and then diethyl ether (500 mL) was added. After shaking, the organic layer was washed with brine (150 mL), dried over sodium sulfate and evaporated. The residue was chromatographed on silica gel using 85/15 hexanes/EtOAc as eluent. Fractions containing product were pooled and the solvent removed under reduced pressure to afford the title compound as an orange oil (13.4 g, 78%).

Step C: Preparation of 5-(2,4-Difluorophenoxy)-1-(2-fluoro-2-methylpropyl)-1H-indazole-6-carboxylic acid: A solution of 6-Bromo-5-(2,4-difluorophenoxy)-1-(2-fluoro-2-methylpropyl)-1H-indazole (15.9 g, 39.8 mmol) in 9:1 methanol:water (300 mL) was degassed for 10 min with an ultrasonic bath. Carbon monoxide gas was then bubbled through the solution for 2 min. To the resulting solution was added, successively, potassium carbonate (16.5 g, 119 mmol), 1,3-bis(diphenylphosphino)propane (0.82 g, 1.99 mmol), and palladium(II) acetate (0.45 g, 1.99 mmol). A balloon of CO with a purge valve was attached to the reaction flask, and the flask was evacuated and recharged five times with CO, and kept under balloon pressure of CO. The flask was heated in an oil bath set to 60° C. and stirred for 17 hr. The mixture was then cooled in an ice bath and acidified with 6M HCl to an apparent pH of <2. The resulting mixture was transferred to a separatory funnel and diluted with ether (500 mL) and water (250 mL). After shaking, the organic layer was stirred with activated charcoal (6 g) at ambient temperature for 15 min, then filtered through a glass microfiber filter to remove the charcoal and palladium residues. The filtrate was extracted with 1M NaOH (300 mL). The aqueous layer was stirred and acidified to pH<2 with conc. HCl. After stirring for a few minutes, a precipitate formed, which was collected by filtration, washed with water, and dried under vacuum to afford the title compound as a light tan powder (10.8 g, 74%).

Step D: Preparation of (S)-5-(2,4-Difluorophenoxy)-1-(2-fluoro-2-methylpropyl)-N-(2-oxopyrrolidin-3-yl)-1H-indazole-6-carboxamide (1k): To a stirred solution of 5-(2,4-Difluorophenoxy)-1-(2-fluoro-2-methylpropyl)-1H-indazole-6-carboxylic acid (16.3 g, 44.7 mmol) in a mixture of DCM (180 mL) and DMF (60 mL) at ambient temperature was added HOBt hydrate (6.85 g, 44.7 mmol). Once all of the HOBt had dissolved, (S)-3-aminopyrrolidin-2-one 4.84 g, 48.3 mmol) was added. To the resulting stirred solution at ambient temperature was added EDC (9.43 g, 49.2 mmol), and the resulting cloudy mixture was stirred at ambient temperature. After stirring for a total of 24 hr the DCM was evaporated under reduced pressure. The residual DMF solution was stirred and diluted with water (300 mL), and the resulting mixture was stirred at ambient temperature. The precipitate that formed was collected by filtration, washed with water, and dried under vacuum to afford the crude product (20.7 g, 104%). This material was combined with a second batch (37.8 g) and recrystallized as follows: The two batches were combined in a 1000 mL Erlenmeyer flask. Acetone (250 mL) was added, and the mixture stirred with gentle heating on a hot plate. All solid dissolved as the solution boiled (52° C.). While the solution was boiling and stirring on the hot plate, hexanes (250 mL, 20° C.) was added slowly from a separatory funnel. Shortly after completion of addition, the product began to crystallize. A second portion of hexanes (250 mL) was added slowly as crystallization continued. The resulting mixture was stored at 2° C. for 14 hr. The crystals that formed were collected by filtration, washed with cold 2:1 hexane:acetone, and dried under vacuum to afford the title compound as an off-white powder (48.2 g, 83% recovery). $^1$H NMR (CDCl$_3$). δ 1.37 (d, J=2.8 Hz, 3H); 1.42 (d, J=3.2 Hz, 3H); 2.02-2.17 (m, 1H); 2.85-2.91 (m, 1H); 3.42-3.46 (m, 2H); 4.53-4.60 (m, 3H); 5.97 (broad s, 1H); 6.88-6.93 (m, 1H); 6.98-7.03 (m, 2H); 7.12-7.18 (m, 1H); 7.90 (s, 1H); 8.20 (d, J=5.2 Hz, 1H); 8.42 (s, 1H). MS (LC/MS/pos): 469.1 (M+Na)$^+$. Chiral purity is >99% ee (done by chiral HPLC).

Example 32

Alternative Synthesis of (S)-5-(2,4-difluorophenoxy)-1-(2-fluoro-2-methylpropyl)-N-(2-oxopyrrolidin-3-yl)-1H-indazole-6-carboxamide (Ik)

Step A: Preparation of 1-(6-Bromo-5-(2,4-difluorophenoxy)-1H-indazol-1-yl)propan-2-one: To a stirred solution of 6-bromo-5-(2,4-difluorophenoxy)-1H-indazole (prepared according to Example 16, Steps A-D; 10.07 g, 31.0 mmol) in DMF (150 mL) at ambient temperature was added cesium carbonate (30.3 g, 92.9 mmol), followed by chloroacetone (5.2 mL, 65.1 mmol). The resulting mixture was vigorously stirred at ambient temperature for 1 hr, then diluted with water (1000 mL). After stirring for 1 hr, the precipitate that formed was collected by filtration, washed with water, and air-dried. This material was dissolved in boiling ethanol (150 mL), and then of water (80 mL) was added. The resulting mixture was cooled at 2° C. for 16 hr. The crystals that formed were collected by filtration, washed with 50/50 water/ethanol, and dried under vacuum to afford the title compound as a light orange powder (8.13 g, 69%).

Step B: Preparation of 1-(6-Bromo-5-(2,4-difluorophenoxy)-1H-indazol-1-yl)-2-methylpropan-2-ol: To a stirred solution of 1-(6-Bromo-5-(2,4-difluorophenoxy)-1H-indazol-1-yl)propan-2-one (3.81 g, 10.0 mmol) in toluene (100 mL) at 21° C. was added a 3.0 M solution of methylmagnesium chloride in THF (5.0 mL, 15 mmol) in one portion. The temperature of the resulting solution rose to 34° C. and was stirred without any temperature control. After a total of 60 min the reaction mixture was quenched by addition of saturated ammonium chloride (50 mL). The resulting mixture was vigorously stirred for 20 min, then transferred to a separatory funnel and shaken. The organic layer was dried over sodium sulfate and the solvent removed under reduced pressure to afford the title compound as an orange oil (3.79 g, 96%) that slowly crystallized on standing.

Step C: Preparation of (S)-5-(2,4-difluorophenoxy)-1-(2-fluoro-2-methylpropyl)-N-(2-oxopyrrolidin-3-yl)-1H-indazole-6-carboxamide (Ik): Prepared from 1-(6-Bromo-5-(2,4-difluorophenoxy)-1H-indazol-1-yl)-2-methylpropan-2-ol according to the method of Example 31, Steps B-D.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:
1. A compound having the formula

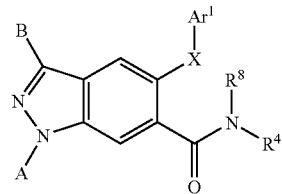

or an enantiomer, diastereomer or pharmaceutically acceptable salt thereof, wherein:

X is O, S, SO, SO$_2$, NR$^7$, C=O, CR$^7$R$^{7a}$, C=NOR$^1$, C=CHR$^1$ or CHOR$^1$;

Ar$^1$ is a 5- or 6-membered aryl or heteroaryl ring, wherein said aryl and heteroaryl are optionally substituted with one or more groups independently selected from NH$_2$, NHMe, NMe$_2$, CH$_2$OH, cyclopropyl, C$_1$-C$_3$ alkyl, C$_1$-C$_3$ haloalkyl, OH, CN, F, Cl, Br I, SCH$_3$, OCH$_3$, and OCF$_3$;

A is H, C$_1$-C$_{12}$ alkyl, C$_2$-C$_{12}$ alkenyl, C$_2$-C$_{12}$ alkynyl, saturated or partially unsaturated cycloalkyl, saturated or partially unsaturated heterocyclyl, aryl or heteroaryl, wherein said alkyl, alkenyl, alkynyl, cycloalkyl, heterocyclyl, aryl and heteroaryl are optionally substituted with one or more groups independently selected from F, Cl, Br, I, CN, =O, =NOR$^{16}$, NR$^{16}$R$^{17}$, NR$^{16}$(C=O)R$^{17}$, NR$^{16}$C(=O)NR$^{17}$R$^{18}$, NR$^{16}$C(=O)R$^{17}$, OC(=O)NR$^{16}$R$^{17}$, CR$^{17}$=NOR$^{16}$, SO$_2$R$^{19}$, SOR$^{17}$, SR$^{17}$, SO$_2$NR$^{16}$R$^{17}$, OR$^{16}$, (C=O)R$^6$, (C=O)OR$^{16}$, O—(C=O)R$^{16}$, C$_1$-C$_6$ alkyl, C$_2$-C$_6$ alkenyl, C$_2$-C$_6$ alkynyl, saturated or partially unsaturated cycloalkyl, saturated or partially unsaturated heterocyclyl, and a 5- or 6-membered heteroaryl or aryl ring;

B is H, NH$_2$, NHMe, NMe$_2$, CH$_3$, CH$_2$OH, cyclopropyl, C$_1$-C$_3$ alkyl, OH, CN, F, Cl, Br or I, wherein said alkyl is optionally substituted with one or more groups independently selected from F, Cl, Br and I;

R$^1$ is H, C$_1$-C$_{12}$ alkyl, C$_2$-C$_{12}$ alkenyl, C$_2$-C$_{12}$ alkynyl;
R$^4$ is

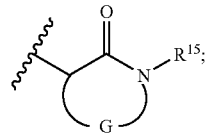

G is a C$_2$-C$_4$ hydrocarbon chain, which taken together with the atoms to which it is attached, forms a 5 to 7 membered saturated or unsaturated ring that is optionally substituted with one or more R$^{30}$ groups;

R$^7$ and R$^{7a}$ are independently H or C$_1$-C$_{12}$ alkyl, or R$^7$ and R$^{7a}$ together with the carbon to which they are attached form a cyclopropyl ring;

R$^8$ is H or Me;

R$^{15}$ is H, C$_1$-C$_6$ alkyl, C$_2$-C$_6$ alkenyl, or C$_2$-C$_6$ alkynyl, wherein said alkyl, alkenyl, and alkynyl are optionally substituted with one or more groups independently selected from F, Cl, Br, I, CN, C$_1$-C$_6$ alkyl, oxo, OH, O—(C$_1$-C$_6$ alkyl), S—(C$_1$-C$_6$ alkyl), NH—(C$_1$-C$_6$ alkyl), N—(C$_1$-C$_6$ alkyl)$_2$, SO—(C$_1$-C$_6$ alkyl), and SO$_2$—(C$_1$-C$_6$ alkyl), or R$^{15}$ is a saturated, partially unsaturated, or fully unsaturated three to seven membered carbocyclic ring or heterocyclic ring having one or two heteroatoms independently selected from O, S and N, wherein said carbocyclic and heterocyclic rings are optionally attached to the nitrogen of the lactam ring through a C$_1$-C$_4$ alkyl, and wherein said carbocyclic and heterocyclic rings are optionally substituted with one or more groups independently selected from F, Cl, Br, I, OH, C$_1$-C$_6$ alkyl, C$_2$-C$_6$ alkenyl, C$_2$-C$_6$ alkynyl, O—(C$_1$-C$_6$ alkyl), S—(C$_1$-C$_6$ alkyl), NH$_2$, oxo, nitro, cyano, C(=O)OH, C(=O)O—(C$_1$-C$_6$ alkyl), NH—(C$_1$-C$_6$ alkyl) and N—(C$_1$-C$_6$ alkyl)$_2$;

R$^{16}$, R$^{17}$ and R$^{18}$ are independently H, C$_1$-C$_6$ alkyl, C$_2$-C$_6$ alkenyl, C$_2$-C$_6$ alkynyl, saturated or partially unsaturated cycloalkyl, saturated or partially unsaturated heterocyclyl, aryl, or heteroaryl, wherein said alkyl, alkenyl, alkynyl, cycloalkyl, heterocyclyl, aryl and heteroaryl are optionally substituted with one or more groups independently selected from F, Cl, Br, I, CN, =O, =NOR$^{21}$, NR$^{21}$R$^{22}$, NR$^{21}$(C=O)R$^{22}$, NR$^{21}$C(=O)NR$^{22}$R$^{23}$, CR$^{22}$=NOR$^{21}$SO$_2$R$^{24}$, SOR$^{22}$, SR$^{22}$, SO$_2$NR$^{21}$R$^{22}$, OR$^{21}$, (C=O)R$^{21}$, (C=O)OR$^{21}$, O—(C=O)R$^{21}$, C$_1$-C$_6$ alkyl, C$_2$-C$_6$ alkenyl, C$_2$-C$_6$ alkynyl, saturated and partially unsaturated cycloalkyl, saturated and partially unsaturated heterocyclyl, and a 5- or 6-membered heteroaryl or aryl ring, or R$^{16}$ and R$^{17}$ together with the atoms to which they are attached form a saturated or partially unsaturated 5-6 membered heterocyclic ring having one or more heteroatoms independently selected from N, O and S, wherein said heterocyclic ring is optionally substituted with one or more groups independently selected from F, Cl, Br, I, CN, =O, =NOR$^{21}$, NR$^{21}$R$^{22}$, NR$^{21}$(C=O)R$^{22}$, NR$^{21}$C(=O)NR$^{22}$R$^{23}$, CR$^{22}$=NOR$^{21}$SO$_2$R$^{24}$, SOR$^{22}$, SR$^{22}$, SO$_2$NR$^{21}$R$^{22}$, OR$^{21}$, (C=O)R$^{21}$, (C=O)OR$^{21}$, O—(C=O)R$^{21}$, C$_1$-C$_6$ alkyl, C$_2$-C$_6$ alkenyl, C$_2$-C$_6$ alkynyl, saturated and partially unsaturated cycloalkyl, saturated and partially unsaturated heterocyclyl, and a 5- or 6-membered heteroaryl or aryl ring, or R$^{17}$ and R$^{18}$ together with the atoms to which they are attached form a saturated or partially unsaturated 5-6 membered heterocyclic ring having one or more heteroatoms independently selected from N, O and S, wherein said heterocyclic ring is optionally substituted with one or more groups independently selected from F, Cl, Br, I, CN, =O, =NOR$^{21}$, NR$^{21}$R$^{22}$, NR$^{21}$(C=O)R$^{22}$, NR$^{21}$C(=O)NR$^{22}$R$^{23}$, CR$^{22}$=NOR$^{21}$SO$_2$R$^{23}$, SOR$^{23}$, SR$^{22}$, SO$_2$NR$^{21}$R$^{22}$, OR$^{21}$, (C=O)R$^{21}$, (C=O)OR$^{21}$, O—(C=O)R$^{21}$, C$_1$-C$_6$ alkyl, C$_2$-C$_6$ alkenyl, C$_2$-C$_6$ alkynyl, saturated or partially unsaturated cycloalkyl, saturated or partially unsaturated heterocyclyl, and a 5-6 membered heteroaryl or aryl ring;

R$^{19}$ is C$_1$-C$_6$ alkyl, C$_2$-C$_6$ alkenyl, C$_2$-C$_6$ alkynyl, saturated or partially unsaturated C$_3$-C$_6$ cycloalkyl, saturated or partially unsaturated C$_1$-C$_6$ heterocyclyl, or a 5-6 membered heteroaryl or aryl ring, wherein said alkyl, alkenyl, alkynyl, cycloalkyl, heterocyclyl, aryl and heteroaryl are optionally substituted with one or more groups independently selected from F, Cl, Br, I, CN, =O =NOR$^{21}$, NR$^{21}$R$^{22}$, NR$^{21}$(C=O)R$^{22}$, NR$^{21}$C(=O)NR$^{22}$R$^{23}$, CR$^{22}$=NOR$^{21}$SO$_2$R$^{23}$, SOR$^{23}$, SR$^{22}$, SO$_2$NR$^{21}$R$^{22}$, OR$^{21}$, (C=O)R$^{21}$, (C=O)OR$^{21}$, O—(C=O)R$^{21}$, C$_1$-C$_6$ alkyl, C$_2$-C$_6$ alkenyl, C$_2$-C$_6$ alkynyl, saturated or partially unsaturated C$_3$-C$_6$ cycloalkyl, saturated or partially unsaturated C$_1$-C$_6$ heterocyclyl, and a 5-6 membered heteroaryl or aryl ring;

R$^{21}$, R$^{22}$ and R$^{23}$ are independently H, C$_1$-C$_6$ alkyl, C$_2$-C$_6$ alkenyl, or C$_2$-C$_6$ alkynyl, wherein said alkyl, alkenyl, and alkynyl are optionally substituted with one or more groups independently selected from F, Cl, Br and I;

R$^{24}$ is C$_1$-C$_6$ alkyl, C$_2$-C$_6$ alkenyl, or C$_2$-C$_6$ alkynyl, wherein said alkyl, alkenyl, and alkynyl are optionally substituted with one or more groups independently selected from F, Cl, Br, and I; and each R$^{30}$ is independently F, C$_1$-C$_6$ alkyl, C$_2$-C$_6$ alkenyl, C$_2$-C$_6$ alkynyl, a saturated or partially unsaturated 3-6 membered carbocyclic ring, a 6 membered aryl ring, or a 5-6 membered heterocyclic ring having one or two heteroatoms independently selected from O, S and N, wherein said carbocyclic, aryl, and heterocyclic rings are optionally attached to the lactam ring through a C$_1$-C$_4$ alkyl, and wherein said alkyl, alkenyl, alkynyl, carbocyclic ring, aryl ring, and heterocyclic ring are optionally substituted with one or more groups independently selected from oxo, OH, SH, NH$_2$, F, Cl, Br, I, CN, C$_1$-C$_6$ alkyl, C$_2$-C$_6$ alkenyl, O—(C$_1$-C$_6$ alkyl), S—(C$_1$-C$_6$ alkyl), NH—(C$_1$-C$_6$ alkyl), SO—(C$_1$-C$_6$ alkyl), and SO$_2$—(C$_1$-C$_6$ alkyl), C(=O)OH, and C(=O)O—(C$_1$-C$_6$)alkyl, or two adjacent R$^{30}$ groups together with the atoms to which they are attached form a 6 membered saturated or partially unsaturated carbocyclic ring or a 6 membered aryl ring.

2. The compound of claim 1, wherein B is H.

3. The compound of claim 1, wherein X is O.

4. The compound of claim 1, which is of formula:

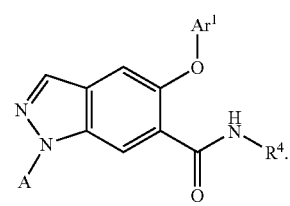

5. The compound of claim 1, wherein R$^4$ is selected from the structures (i)-(v):

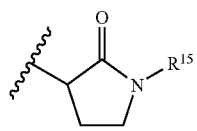
(i)

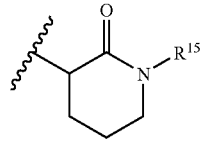
(ii)

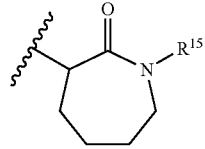
(iii)

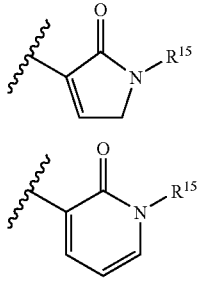

wherein structures (i), (ii), and (iii) are optionally substituted with one to four $R^{30}$ groups, and structures (iv) and (v) are optionally substituted with one to three $R^{30}$ groups.

6. The compound of claim 1; wherein $R^4$ is unsubstituted.

7. The compound of claim 1, wherein $R^{15}$ is H or $C_1$-$C_6$ alkyl, wherein said alkyl is optionally substituted with one or more OH, F, Cl, or Br.

8. The compound of claim 7, wherein $R^{15}$ is H, methyl, or $CH_2CH_2OH$.

9. The compound of claim 1, wherein $Ar^1$ is phenyl optionally substituted with one or more atoms or groups independently selected from F, Cl, Br, I, $OR^{16}$, or $C_1$-$C_6$ alkyl, wherein said alkyl is optionally substituted with one or more groups independently selected from F, C, Br and I.

10. The compound of claim 9, wherein $Ar^1$ is phenyl substituted with one or more F.

11. The compound of claim 9, wherein $Ar^1$ is 2,4-difluorophenyl.

12. The compound of claim 1, wherein A is $C_1$-$C_6$ alkyl optionally substituted with one or more atoms or groups independently selected from F, Cl, Br, I and $OR^{16}$.

13. The compound of claim 12, wherein A is $C_1$-$C_6$ alkyl substituted with one or more atoms or groups independently selected from OH and F.

14. The compound of claim 13, wherein A is

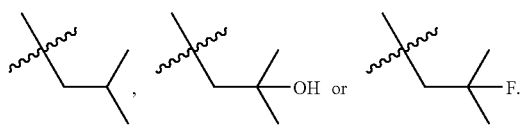

15. The compound of claim 1, wherein $R^4$ is a saturated ring and the lactam carbon in the position alpha to the carbonyl is in the (S) configuration.

16. The compound of claim 1, selected from:
(S)-5-(2,4-difluorophenoxy)-1-isobutyl-N-(2-oxopyrrolidin-3-yl)-1H-indazole-6-carboxamide;
(S)-5-(2,4-difluorophenoxy)-1-isobutyl-N-(2-oxopiperidin-3-yl)-1H-indazole-6-carboxamide;
(S)-5-(2,4-difluorophenoxy)-1-isobutyl-N-(2-oxoazepan-3-yl)-1H-indazole-6-carboxamide;
(S)-5-(2,4-difluorophenoxy)-1-isobutyl-N-(1-methyl-2-oxopyrrolidin-3-yl)-1H-indazole-6-carboxamide;
(S)-5-(2,4-difluorophenoxy)-1-isobutyl-N-(1-methyl-2-oxopiperidin-3-yl)-1H-indazole-6-carboxamide;
(S)-5-(2,4-difluorophenoxy)-1-isobutyl-N-(1-methyl-2-oxoazepan-3-yl)-1H-indazole-6-carboxamide;
(S)-5-(2,4-difluorophenoxy)-N-(1-(2-hydroxyethyl)-2-oxopyrrolidin-3-yl)-1-isobutyl-1H-indazole-6-carboxamide;
(S)-5-(2,4-difluorophenoxy)-N-(1-(2-hydroxyethyl)-2-oxopiperidin-3-yl)-1-isobutyl-1H-indazole-6-carboxamide;
(S)-5-(2,4-difluorophenoxy)-N-(1-(2-hydroxyethyl)-2-oxoazepan-3-yl)-1-isobutyl-1H-indazole-6-carboxamide;
(S)-5-(2,4-difluorophenoxy)-1-(2-hydroxy-2-methylpropyl)-N-(2-oxopyrrolidin-3-yl)-1H-indazole-6-carboxamide;
(S)-5-(2,4-difluorophenoxy)-1-(2-fluoro-2-methylpropyl)-N-(2-oxopyrrolidin-3-yl)-1H-indazole-6-carboxamide;
(S)-5-(2,4-difluorophenoxy)-1-(2-fluoro-2-methylpropyl)-N-(2-oxopiperidin-3-yl)-1H-indazole-6-carboxamide;
(S)-5-(2,4-difluorophenoxy)-1-(2-fluoro-2-methylpropyl)-N-(2-oxoazepan-3-yl)-1H-indazole-6-carboxamide, and pharmaceutically acceptable salts thereof.

17. The compound of claim 1, which is (S)-5-(2,4-difluorophenoxy)-1-(2-fluoro-2-methylpropyl)-N-(2-oxopyrrolidin-3-yl)-1H-indazole-6-carboxamide, or a pharmaceutically acceptable salt thereof.

18. A pharmaceutical composition comprising a compound according to claim 1 and a pharmaceutically acceptable carrier.

19. A method of preparing a compound as defined in claim 1, comprising coupling a compound having the formula (II)

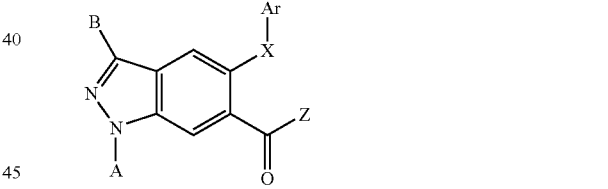

in which Z represents OH or a leaving atom or group, with a compound having the formula $$HNR^{8a}R^4 \quad (III)$$

wherein $R^{8a}$ is $R^8$ or an amine protecting group;
followed by removing any amine protecting group and, if desired, forming a salt.

* * * * *